(12) United States Patent
Stierli et al.

(10) Patent No.: US 8,623,902 B2
(45) Date of Patent: Jan. 7, 2014

(54) MICROBIOCIDES

(75) Inventors: Daniel Stierli, Stein (CH); Harald Walter, Stein (CH); Sebastian Wendeborn, Stein (CH); Antoine Daina, Geneva (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 406 days.

(21) Appl. No.: 13/000,181

(22) PCT Filed: Jun. 9, 2009

(86) PCT No.: PCT/EP2009/057099
§ 371 (c)(1),
(2), (4) Date: Mar. 25, 2011

(87) PCT Pub. No.: WO2009/153191
PCT Pub. Date: Dec. 23, 2009

(65) Prior Publication Data
US 2011/0207781 A1   Aug. 25, 2011

(30) Foreign Application Priority Data
Jun. 20, 2008   (GB) .................................. 0811451.4

(51) Int. Cl.
*A61K 31/4155* (2006.01)
*C07D 403/02* (2006.01)

(52) U.S. Cl.
USPC ........................................ 514/406; 548/364.1

(58) Field of Classification Search
None
See application file for complete search history.

(56) References Cited

U.S. PATENT DOCUMENTS

2003/0195195 A1* 10/2003 Haviv et al. .................. 514/218

FOREIGN PATENT DOCUMENTS

| EP | 0405808 | 1/1991 |
|---|---|---|
| WO | 2007141009 | 12/2007 |

OTHER PUBLICATIONS

Elliott, R. L. et al: "2-(Aryloxymethyl) azacyclic analogues as novel nicotinic acetylcholine receptor (nA ChR) ligands", Bioorganic & Medicinal Chemistry Letters, Pergamon, Elsevier Science, GB, vol. 6, No. 19, Oct. 8, 1996, pp. 2283-2288.
Starr, D. F. et al: "Electron—sharing ability of organic radicals. VI. alpha.-Substituted pyrrolines and pyrrolidines", Journal of the American Chemical Society, 54, pp. 3971-3976, (1932).
Hess, K. et al: "Action of aldehydes on hydramines of the pyrrolidene and piperidine series. IV. A method for alkylating secondary amino alcohols", Berichte Der Deutschen Chemischen Gesellschaft, 50, pp. 344-351, (1917).
Lowe, Gordon et al: "Synthesis and configurational assignment of some novel bicyclic sulfamidites and sulfamidates" Tetrahedrom: Asymmetry, 1(12), pp. 885-894, (1990).
Scarso, A. et al: "Synthesis and biological activities of bradykinin analogs with .PSI.(E,CH:CH) and .PSI.(CH2NH) isosteric peptide bond replacements", Bulletin Des Societes Chimiques Belges 100(5), pp. 381-399, (1991).
Bigi, Franca et al: "Highly regio-and diastereoselective Friedel—Crafts alkylation of phenols with .alpha.-amino aldehydes. Synthesis of optically active ephedrine-like compounds" Tetrahedron Letters, 30(9), pp. 1121-1124, (1989).

* cited by examiner

*Primary Examiner* — Michael Barker
(74) *Attorney, Agent, or Firm* — R. Kody Jones

(57) ABSTRACT

Compounds of Formula (I), in which the substituents are as defined in claim 1, are suitable for use as microbiocides.

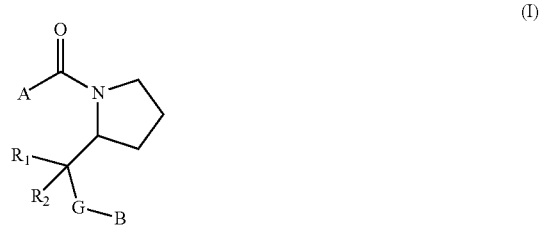

11 Claims, No Drawings

MICROBIOCIDES

This application is a 371 of International Application No. PCT/EP2009/057099 filed Jun. 9, 2009, which claims priority to GB 0811451.4 filed Jun. 20, 2008, the contents of which are incorporated herein by reference.

The present invention relates to novel microbiocidally active, in particular fungicidally active, proline amides. It further relates to intermediates used in the preparation of these compounds, to compositions which comprise these compounds and to their use in agriculture or horticulture for controlling or preventing infestation of plants by phytopathogenic microorganisms, preferably fungi.

Certain proline, piperidine and morpholine derivatives as orexin receptor antagonists are described in WO 02/089800. It has been found that novel proline amides have microbiocidal activity.

The present invention accordingly relates to compounds of formula I

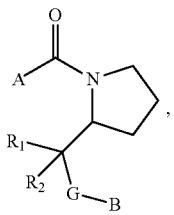

wherein
A is a pyrazole or pyridine ring substituted by one or more substituents selected from the group consisting of $C_1$-$C_4$alkyl, $C_1$-$C_4$haloalkyl and halogen; $R_1$ and $R_2$ independently of each other, are hydrogen, hydroxy, halogen or $C_1$-$C_6$alkyl; or $R_1$ and $R_2$ together is C=O or C=N(O—$C_1$-$C_6$alkyl);
B is phenyl which can be substituted by one or more substituents selected from the group consisting of halogen, $C_1$-$C_6$alkyl, $C_3$-$C_6$cycloalkyl, $C_1$-$C_6$haloalkyl, —C($C_1$-$C_4$alkyl)=N—O—$C_1$-$C_6$alkyl or —C(H)=N—O—$C_1$-$C_6$alkyl; and
G is oxygen, sulphur, $CH_2$, $(CH_2)_2$ or a bond;
and tautomers/isomers/enantiomers of these compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl.

In the context of the present invention "substituted by one or more substituents" in the definition of the substituents, means typically, depending on the chemical structure of the substituents, monosubstituted to seven-times substituted, preferably monosubstituted to five-times substituted, more preferably mono-, double- or triple-substituted.

Halogen is generally fluorine, chlorine, bromine or iodine, preferably fluorine, chlorine or bromine. This also applies, correspondingly, to halogen in combination with other meanings, such as halogenalkyl or halogenalkoxy. Halogenalkyl groups preferably have a chain length of from 1 to 4 carbon atoms. Halogenalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

In a preferred group of compounds of formula I,
A is the group $A_1$

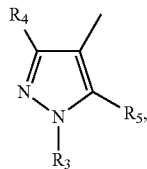

wherein
$R_3$ is methyl; $R_4$ is $C_1$-$C_4$haloalkyl, preferably difluoromethyl or trifluoromethyl and
$R_5$ is hydrogen or A is the group $A_2$

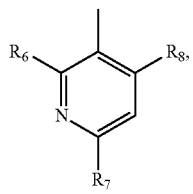

wherein
$R_6$ and $R_8$, independently from each other, are hydrogen, methyl or chloro; and
$R_7$ is hydrogen, methyl, chloro or —C(H)=N—O—$CH_3$.
Preferably, $R_1$ and $R_2$ are hydrogen; or $R_1$ and $R_2$ together are C=O or C=N(O—$C_1$-$C_6$alkyl).

In further preferred compounds of formula I, G is oxygen or a bond.

Further preferred compounds of formula I are represented by the compounds of formula Ia,

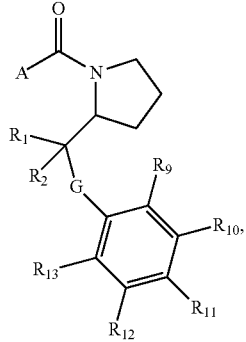

wherein
A, $R_1$, $R_2$ and G are as defined under formula I above and $R_9$, $R_{10}$, $R_{11}$, $R_{12}$ and $R_{13}$ independently from each other, are hydrogen, halogen, $C_1$-$C_6$alkyl, $C_1$-$C_6$haloalkyl or C(H) NO—$C_1$-$C_6$alkyl. Preferred compounds from this group are those, wherein $R_9$, $R_{10}$, $R_{11}$, $R_{12}$ and $R_{13}$ independently from each other, are hydrogen, halogen, $C_1$-$C_6$alkyl or C(H)NO—$C_1$-$C_6$alkyl. In further preferred compounds of formula Ia, $R_1$ and $R_2$ independently of each other, are hydrogen, hydroxy or $R_1$ and $R_2$ together is C=O or C=N(O—$C_1$-$C_6$alkyl). Especially preferred are compounds of formula Ia, wherein G is oxygen or a bond.

Compounds of formula I may be prepared by reacting a compound of formula II or a salt thereof

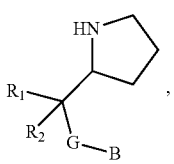

(II)

in which B, G, $R_1$ and $R_2$ are as defined under formula I, with a compound of formula III $$A—C(=O)—R^* \quad (III),$$

in which A is as defined under formula I, and R* is halogen, hydroxy, or $C_1$-$C_6$alkoxy, preferably chloro, in the presence of a base, such as triethylamine, Hunig base, sodium bicarbonate, sodium carbonate, potassium carbonate, pyridine or quinoline, preferably triethylamine, and in a solvent, such as diethylether, TBME, THF, dichloromethane, chloroform, DMF or NMP, for between 10 minutes and 48 hours, preferably 12 to 24 hours, and between temperatures of from 0° C. and reflux, preferably 20 to 25° C. When R* is hydroxy, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI), may be used.

Intermediates of the formula II, in which B, $R_1$ and $R_2$ are as defined under formula I; may be prepared according to the following reaction schemes (schemes 1 to 5) or in analogy to those reaction schemes.

Chiral Intermediates of formula (S)-IIa

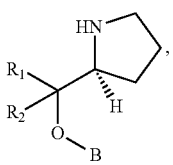

S-(IIa)

in which B, $R_1$ and $R_2$ are as defined under formula I, may be prepared as described in reaction scheme 1 and 2.

Chiral bi-cyclic sulfamidates of formula V, in which $R_1$, and $R_2$ are as defined under formula I, may be prepared by reacting an aminoalcohol of formula IV with sulfuryl chloride in the presence of base. Suitable bases include organic amine, e.g., triethylamine or preferably, pyridine. The reactants are mixed in a suitable aprotic solvent, such as methylene chloride, 1,2-dichloroethane, carbon tetrachloride, benzene, toluene or pyridine, and stirred for 5 to 60 minutes at or below −60° C. The reaction mixture is gradually allowed to warm, with stirring, until reaction is complete, e.g. to −40° C. for 1 to 3 hours, then to 0° C. for 30 to 60 minutes. Alternatively, a chiral bi-cyclic sulfamidites of formula VI may be prepared by reacting an aminoalcohol of formula IV with thionyl chloride. This cyclisation reaction may be performed in the presence of a base. A suitable base is pyridine. Suitable solvents include dichloromethane and nitriles such as acetonitrile and propionitrile. The reaction temperature typically lies in the range of −50° C. to 20° C.

Chiral bi-cyclic sulfamidates of formula V, in which A, $R_1$ and $R_2$ are as defined under formula Ib, may be prepared by oxidation of the cyclic sulfamidites of formula VI. Suitable oxidation reagents are $RuO_4$ and $RuCl_3 \cdot 3H_2O$ in combination with $NaIO_4$. Suitable solvents include mixtures of nitriles and water; as nitrile can be used, for example, acetonitrile or propionitrile. The reaction temperature typically lies in the range of 0° C. to 30° C.

For a review of preparation methods for cyclic sulfates and sulfamidates, see Lohray, B. B. in *Advances in Heterocyclic Chemistry*; Katritzky, A. R., Ed.; Academic Press: San Diego, 1997; Vol. 68, pp 89-180; and Posakony J. J., *J. Org. Chem.*, 2002, 67, 5164-5169. The cyclic sulfamidates of formula V may then react with compounds of formula VII, in which B is as defined under formula I, to form compounds of formula VIII. This ring-opening by using oxygen nucleophiles may be performed in the presence of a base. Suitable bases include carbonates, cesium carbonate, potassium carbonate, or metal hydrides, such as sodium hydride and lithium hydride. Suitable solvents include ethers such as tetrahydrofuran diethyl ether, etc. The solvent is then evaporated, and the remaining sulfamic acid salt of formula VIII is hydrolyzed with aqueous acid to form the amine of formula IIa, which may be isolated as the free amine or as an acid addition salt.

Scheme 1:

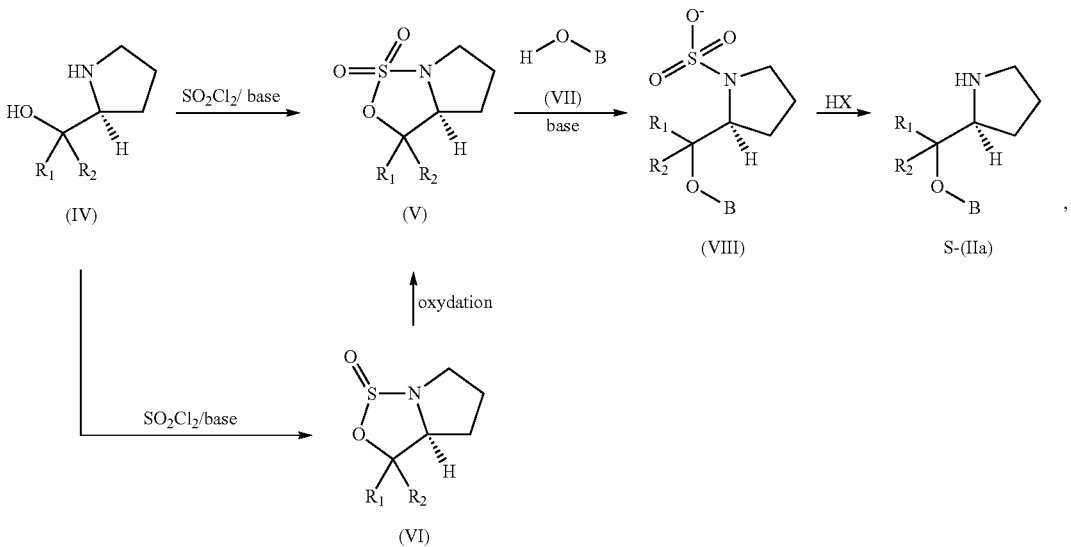

Scheme 2:

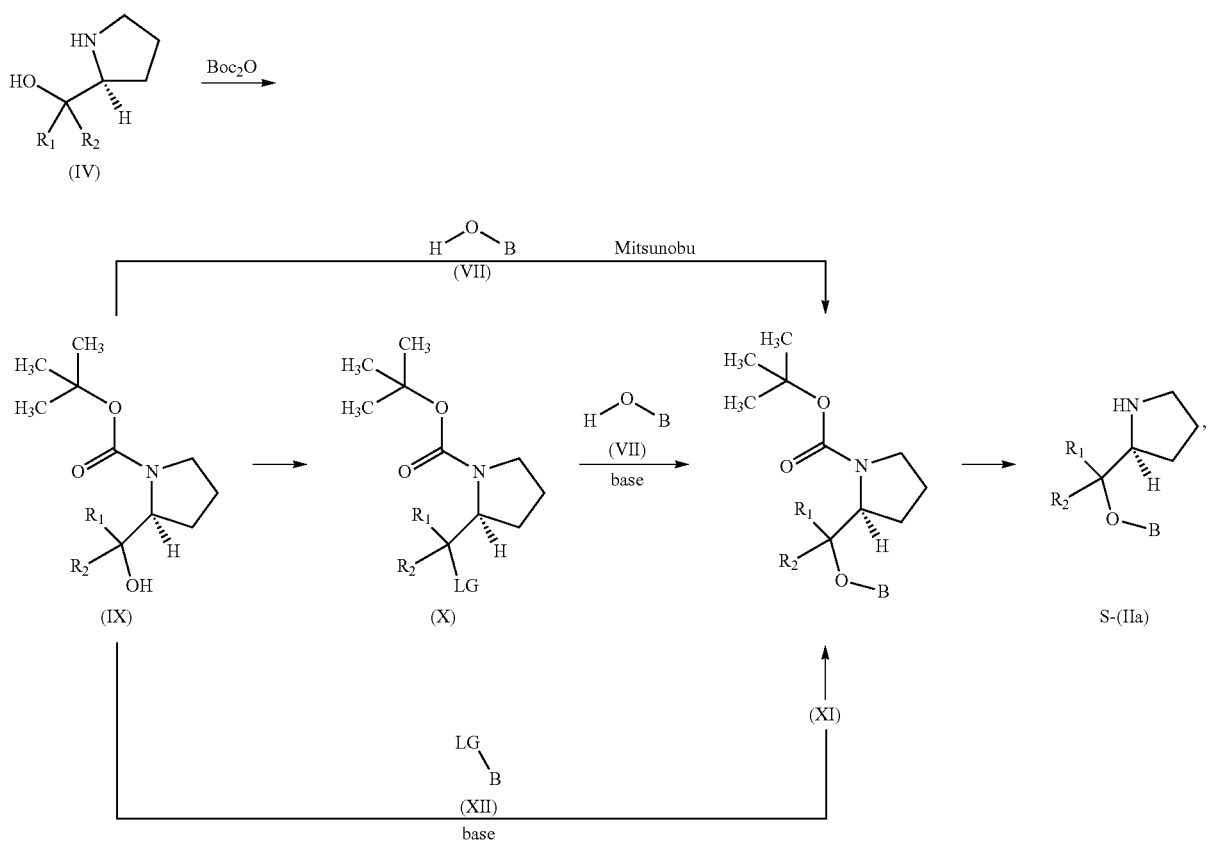

N-protected aminoalcohol of formula IX, in which $R_1$ and $R_2$ are as defined under formula II, can be prepared by known methods starting from aminoalcohol of formula IV. Compounds of formula XI, in which B, $R_1$ and $R_2$ are as defined under formula II, can be directly prepared by the reaction—as described by Mitsunobu (O. Mitsunobu, Synthesis, 1981, 1-28)—from the N-protected aminoalcohol of formula IX and VII in the presence of 1-2 equivalents of triphenylphosphine and 1-2 equivalents dialkylazodicarboxylate, such as diethylazodicarboxylate or diisopropylazodicarboxylate. The reaction is generally run in an inert solvent, such as tetrahydrofurane or dichloromethane, at a temperature range of 0° C. to 20° C.

Compounds of formula XI can also be prepared from the N-protected aminoalcohol of formula IX via compounds of formula X, in which $R_1$ and $R_2$ are as defined under formula II, and LG stands for a leaving group. Typical leaving groups are chloride, bromide, iodide, (methylsulfonyl)oxy or [(4-methylphenyl)sulfonyl]oxy. Standard methods for the conversion of alcohols to halides are described in: March, J. Advanced Organic Chemistry; J. Wicly & Sons: New York, (1992); $4^{th}$ Ed, pp 498-499. In such a reaction, the leaving group LG is displaced in the presence of an acid acceptor, which can be a tertiary amine, such as triethylamine, an alkoxyde, such as potassium t-butoxyde, a carbonate, such as potassium carbonate or metal hydrides, such as sodium hydride and lithium hydride. The displacements can be carried out in inert polar aprotic solvents, such as dimethylformamide or dimethylsulfoxide, ether solvents, such as tetrahydrofurane or dioxane. Reaction temperature typically lies in the range of from 20° C. to 150° C.

Alternatively compounds of formula XI may be prepared by the reaction of a compound of formula IX and a compound of formula XII, while using the displacement conditions described above for the transformation of compounds of formula X into compounds of formula XI. This nucleophilic substitution reaction may preferably be used in the case that the compound of formula XII is an activated halogen-aromatic compound. In the case that the compound of formula XII is a non-activated compound, said reaction may be carried out under palladium- or copper-catalyst mediated conditions.

Intermediates of formula IIb

wherein B, $R_1$ and $R_2$ are as defined under formula I and n is 0, 1 or 2; may be prepared as described in reaction scheme 3.

Scheme 3:

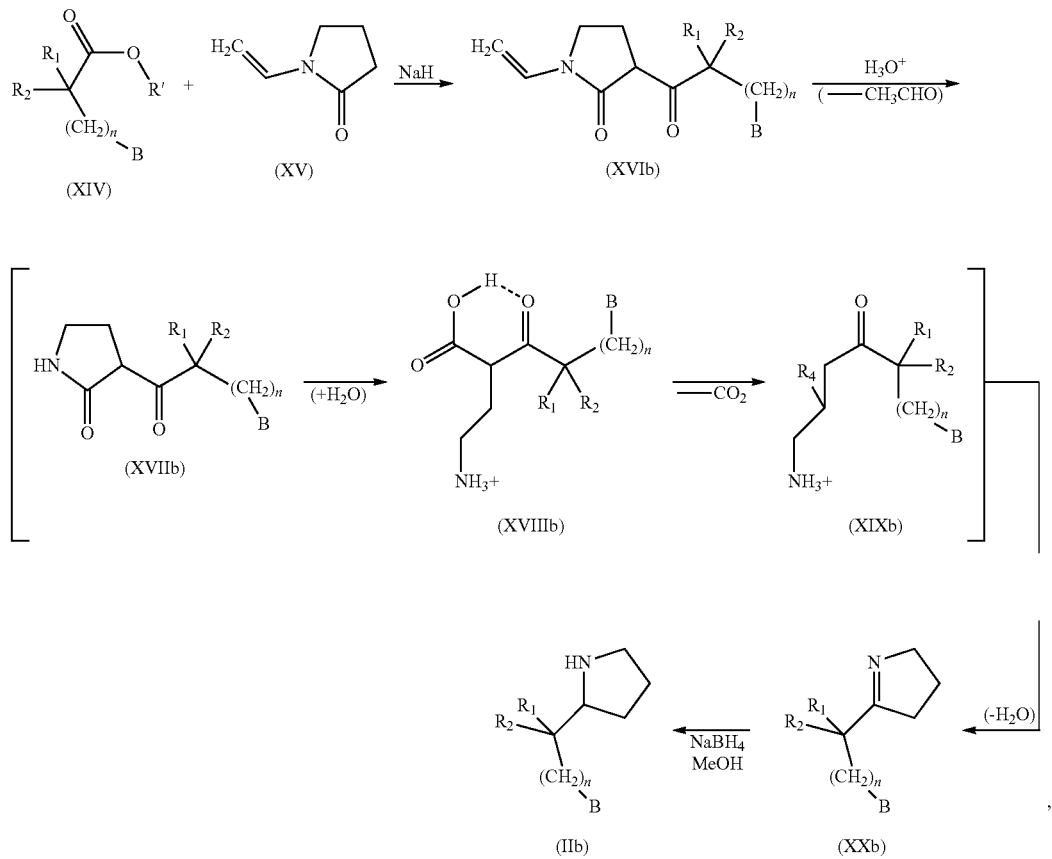

Keto lactam intermediates of formula XVIb, in which $R_1$, $R_2$ and B are as defined under formula I, may be prepared by reacting an ester of formula XIV with N-vinylpyrrolidinone of formula XV in the presence of metal hydrides, such as sodium hydride and lithium hydride. The acylation can be carried out in aprotic solvents, such as tetrahydrofurane or toluene. The reaction temperature typically lies in the range of from 20° C. below to reflux temperature. Pyrroline derivatives of formula XXb may be generated using a modification of the procedure of Brandage and Lindblom (Acta Chem. Scand. B, 1976, 30, 93) by the acidmediated hydrolysis, decarboxylation and cyclisation of keto lactam of formula XVIb. Hydrolysis, decarboxylation and cyclisation can be conducted by slow addition of keto lactam of formula XVIb to refluxing 6N HCl. Amines of formula IIb can then be prepared by reaction of compounds of formula XXb with a reducing reagent such as sodium borohydride and potassium borohydride. The reaction can be performed in protic solvents, such as alcohols methanol, ethanol, isopropanol or tert-butanol. The reaction temperature typically lies in the range of −5° C. to 30° C.

Compounds of formula XVIc may be prepared by alkylation of XVIb with an alkyl halide in the presence of metal hydrides, such as sodium hydride and lithium hydride. The alkylation can be carried out in aprotic solvents, such as tetrahydrofurane or toluene. The reaction temperature typically lies in the range of −5° C. to 40° C. Amines of formula IIc can then be prepared in analogy using the same methodology described for the preparation of compounds of formula XXb and IIb.

Intermediates of formula IId

(IId)

in which B is as defined under formula I may be prepared as described in reaction scheme 4.

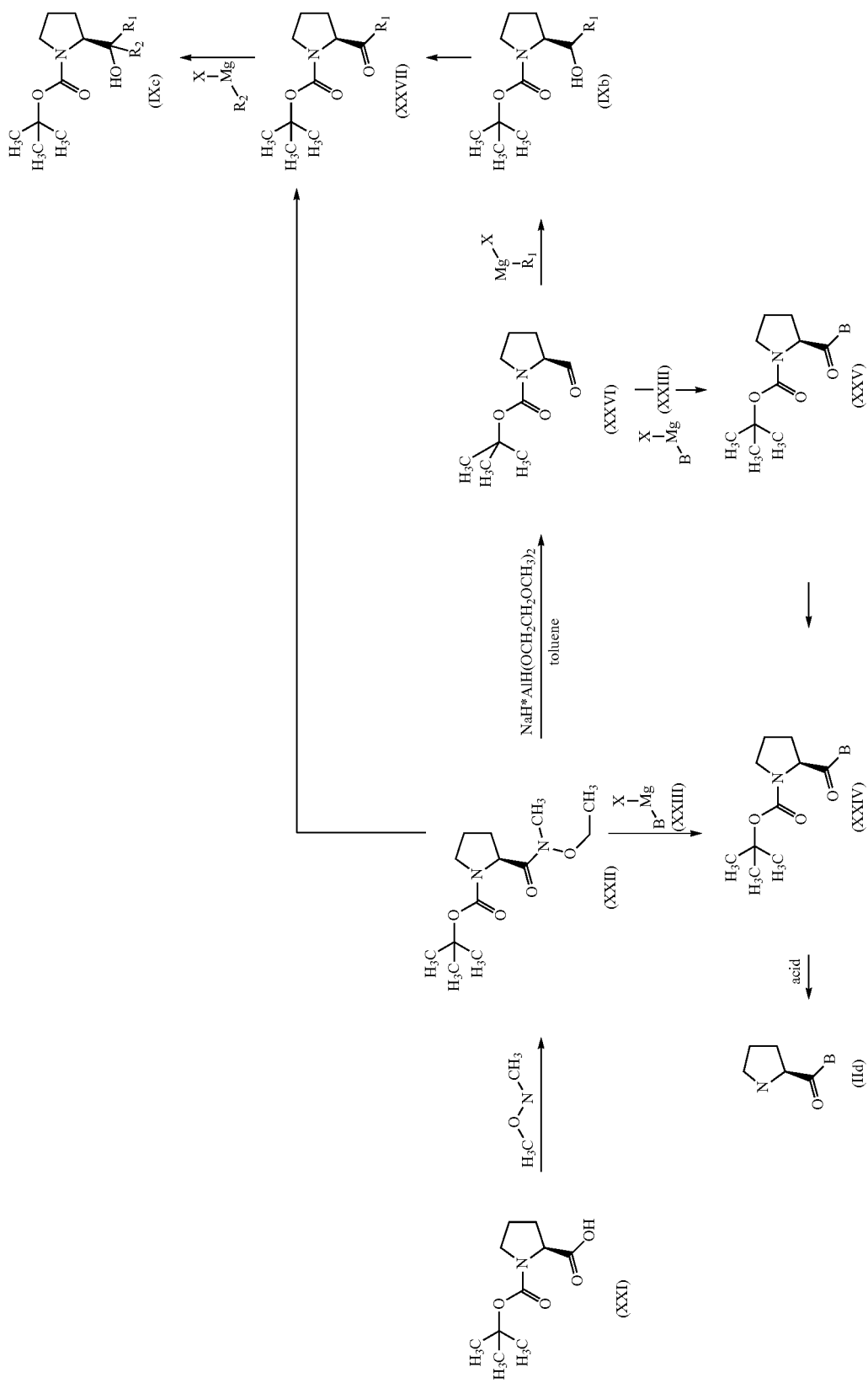
Scheme 4:

Weinreb amide of the formula XXII may be prepared by reacting a N-protected aminoacid of formula XXI, with N,O-dimethylhydroxylamine or a salt thereof using a coupling agent, such as benzotriazol-1-yloxytris(dimethylamino)phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CDI).

A subsequent reaction of the Weinreb amide of the formula XXII with a Grignard reagent of the formula XXIII, wherein B is as defined under formula II, yields the ketone of formula XXIV, which can be converted to a compound of formula IId by deprotection of the Boc group. The Boc group can be conveniently removed in the presence of a strong acid, such as trifluoroacetic acid in dichloromethane to yield the amines of formula IId. The ketone intermediates of formula XXIV may be also prepared by oxidizing an alcohol of formula XXV. Advantageous oxidation procedures can be based on sulphur oxidation agents (in the literature referred to, for example, as Swern-oxidation or analogous oxidations), metal based oxidation agents or hydrogen peroxide in the presence of metal catalysts, such as $Na_2WO_4$ (c.f. e.g. R. Noyori, Bull. *Chem. Soc. Jpn.* 1999, 72, 2287-2306). Compounds of formula XXV may be prepared by the reaction of compounds of formula XXVI with a Grignard reagent of formula XXIII.

Aldehyde of formula XXVI may be prepared by the reduction of compound of formula XII using Vitride (sodium bis(2-methoxyethoxy)aluminium hydride) in toluene at temperatures between −50° C. to −10° C.

In addition intermediates of formula IXb and IXc may be also prepared from a compound of formula XXII, using the same methodology described above.

Compounds of formula Id

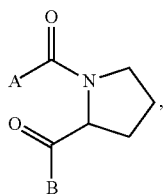

(Id)

in which A and B are defined under formula I may be prepared and further converted in novel compounds of formula Ie, If, Ig as described in reaction scheme 5, by known methods. See preparation examples P5 to P7.

Scheme 5:

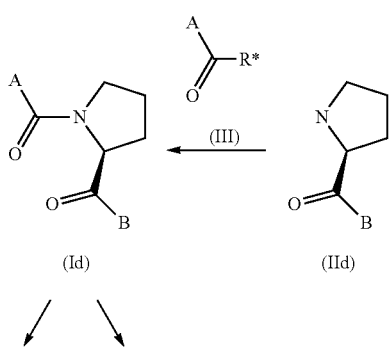

The compounds of the formulae IV, VII, XII, XIII, XV and XXI, wherein the substituents as described above, are known and commercially available or can be prepared according to the above-mentioned references or according to methods known in the art.

The compounds of the formula III and IIIb, wherein the substituents as described above, are known and partially commercially available. They can be prepared analogously as described, for example, in WO 00/09482, WO 02/38542, WO 04/018438, EP-0-589-301, WO 93/11117 and Arch. Pharm. Res. 2000, 23(4), 315-323.

For preparing all further compounds of the formula I functionalized according to the definitions of A, B, G, $R_1$, $R_2$, and $R_3$, there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The reactions to give compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

The compounds I and, where appropriate, the tautomers thereof, can, if appropriate, also be obtained in the form of hydrates and/or include other solvents, for example those which may have been used for the crystallization of compounds which are present in solid form.

The intermediates of formula II

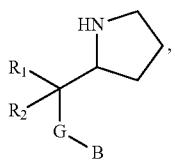
(II)

in which B, G, $R_1$ and $R_2$ are as defined under formula I, are novel and are developed specifically for the preparation of the compounds of the formula I. Accordingly, said intermediates also represent an object of the present invention.

The intermediates of formula IV

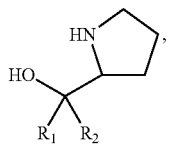
(IV)

in which $R_1$, and $R_2$ are as defined under formula I, are novel and are developed specifically for the preparation of the compounds of the formula I. Accordingly, said intermediates also represent an object of the present invention.

The intermediates of formula V

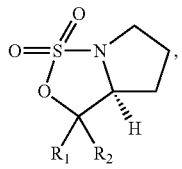
(V)

in which $R_1$ and $R_2$ are as defined under formula I, are novel and are developed specifically for the preparation of the compounds of the formula I. Accordingly, said intermediates also represent an object of the present invention.

The intermediate of formula XXII

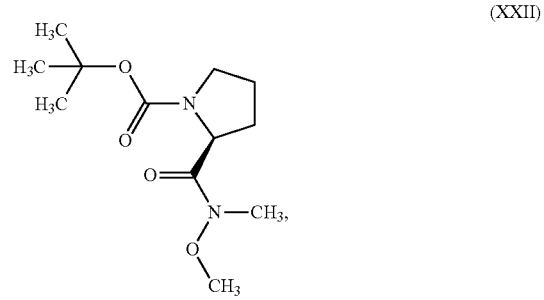 [SMILES: CON(C)C(=O)[C@@H]1CCCN1C(=O)OC(C)(C)C]
(XXII)

is novel and was developed specifically for the preparation of the compounds of the formula I. Accordingly, said intermediate also represents an object of the present invention.

The intermediate of formula XXVI

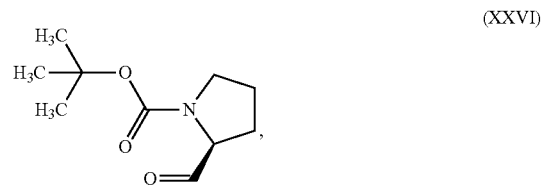
(XXVI)

is novel and was developed specifically for the preparation of the compounds of the formula I. Accordingly, said intermediate also represents an object of the present invention.

It has now been found that the compounds of formula I according to the invention have, for practical purposes, a very advantageous spectrum of activities for protecting useful plants against diseases that are caused by phytopathogenic microorganisams, such as fungi, bacteria or viruses.

The invention relates to a method of controlling or preventing infestation of useful plants by phytopathogenic microorganisms, wherein a compound of formula I is applied as acitve ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis*, *Pyricularia*, *Helminthospo-* rium, *Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB (b1) toxin); Starlink® (maize variety that expresses a Cry9(c) toxin); Herculex I® (maize variety that expresses a CryIF(a2) toxin and the enzyme phosphinothricin N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as acitve ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as acitve ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as acitve ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp,

PREPARATION EXAMPLES

Example P1

Preparation of 3-difluoromethyl-1-methyl-1H-pyrazol-4-yl)-[(S)-2-(2,6-dimethyl-phenoxymethyl)-pyrrolidin-1-yl]-methanone (compound 1.225)

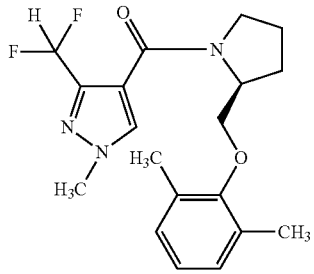 [SMILES: Cc1cccc(C)c1OC[C@@H]1CCCN1C(=O)c1cn(C)nc1C(F)F]

A mixture of (3-difluoromethyl-1-methyl-1H-pyrazol-4-yl)-((S)-(2-hydroxymethyl-pyrrolidin-1-yl)-methanone (2.0 g; 7.7 mmol), which was prepared as described in example P8, triphenylphosphine (2.1 g; 8.0 mmol) and 2,6-dimethylphenol (0.94 g; 7.7 mmol) in dry THF (30 ml) was cooled in an ice-bath. Diisopropyl azocarboxylate (1.60 g; 8.0 mmol) in dry THF (15 ml) was added dropwise, with stirring under nitrogen atmosphere over 10 minutes. The reaction mixture was stirred at ambient temperature for 6 hours. After removal of the solvent in vacuo, the residue (6.81 g) was purified by flash chromatography using silica gel (eluent: cyclo hexane/ethyl acetate 2:8). 1.31 g (46.8% of theory) of 3-difluoromethyl-1-methyl-1H-pyrazol-4-yl)-[(S)-2-(2,6-dimethyl-phenoxymethyl)-pyrrolidin-1-yl]-methanone (compound 1.225) was obtained in form of a white solid m.p. 137-140° C.

$^1$H NMR (400 MHz, CDCl$_3$): δ 1.92-1.99 (m, 1H), 2.15-2.24 (m, 2H), 2.22 (s, 6H, 2×CH$_3$), 2.38-2.46 (m, 1H), 3.62-3.70 (m, 2H), 3.85-3.94 (m, 1H), 3.96 (s, 3H, NCH$_3$), 4.09-4.12 (m, 1H), 4.59-4.62 (m, 1H), 6.90-7.15 (m, 3H, Ar—H, t, 1H, CHF$_2$), 7.60 (s, 1H). MS [M+H]$^+$ 364. $[\alpha]^{20}_D$=−68.3 (c 5.75, CHCl$_3$).

Example P2a

Preparation of 3-difluoromethyl-1-methyl-1H-pyrazol-4-yl)-[(S)-2-(2,4,6-trichloro-phenoxymethyl)-pyrrolidin-1-yl]-methanone (compound 1.006)

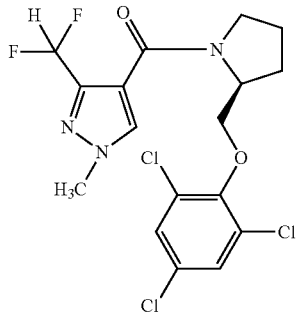 [SMILES: Cn1cc(C(=O)N2CCC[C@H]2COc2c(Cl)cc(Cl)cc2Cl)c(C(F)F)n1]

At a temperature of 0° C., a solution of 3-difluoromethyl-1-methyl-1H-pyrazole-4-carbonyl chloride (0.243 g; 1.24 mmol) in dichloromethane (5 ml) was added dropwise to a stirred solution of (S)-2-(2,4,6-trichloro-phenoxymethyl)-pyrrolidine hydrochloride (0.35 g; 1.24 mmol), which was prepared as described in example P12, and triethylamine (0.35 ml; 2.48 mmol) in dichloromethane (10 ml). The ice bath was removed and reaction mixture was allowed stirring for 3 hours. The reaction mixture was washed with 1M NaOH (10 ml), 2M HCl (10 ml) and saturated NaCl (50 ml) and then dried over Na$_2$SO$_4$. After removal of the solvent, the residue (0.45 g in the form of an oil) was purified by flash chromatography over silica gel (eluent:cyclohexane/ethyl acetate 2:8). 0.27 g (50% of theory) of 3-difluoromethyl-1-methyl-1H-pyrazol-4-yl)-[(S)-2-(2,4,6-trichloro-phenoxymethyl)-pyrrolidin-1-yl]-methanone was obtained in form of an oil which solified after standing.

$^1$H NMR (400 MHz, CDCl$_3$): δ 1.92-1.99 (m, 1H), 2.16-2.22 (m, 2H), 2.38-2.46 (m, 1H), 3.64-3.69 (m, 2H), 3.96 (s, 3H, NCH$_3$), 4.18-4.22 (m, 1H), 4.31-4.34 (m, 1H), 4.59-4.62 (m, 1H), 6.96-7.24 (t, 1H, CHF$_2$), 7.28 (s, 2H, Ar—H), 7.60 (s, 1H). MS [M+H]$^+$ 338/340/342. $[\alpha]^{24}_D$=−54.2 (c 5.0, CHCl$_3$).

Example P2b

Preparation of 3-difluoromethyl-1-methyl-1H-pyrazol-4-yl)-[(S)-2-(2,4,6-trichloro-phenoxymethyl)-pyrrolidin-1-yl]-methanone (compound 1.006)

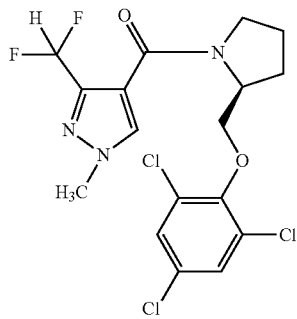 [SMILES: Cn1cc(C(=O)N2CCC[C@H]2COc2c(Cl)cc(Cl)cc2Cl)c(C(F)F)n1]

At ambient temperature, sodium hydride 55% in oil (62 mg, 1.4 mmol) was added over 5 minutes to a solution of 2,4,6-trichlorophenol (0.28 g, 1.4 mmol) in DMF (5 ml). The reaction mixture was stirred 15 minutes, then a solution of ((S)-2-chloromethyl-pyrrolidin-1-yl)-(3-difluoromethyl-1-methyl-1H-pyrazol-4-yl)-methanone (0.43 g, 1.55 mmol), which was prepared as described in example P9, in DMF (5 ml) was added. The reaction mixture was stirred for 2 hours, at ambient temperature. The reaction mixture was heated to 70° C. and stirred for another 15 hours. After cooling the reaction mixture was poured on 1N HCl (40 ml) and then extracted with ethyl acetate (2×40 ml). The organic layers was washed with saturated NaCl (50 ml) and then dried over Na$_2$SO$_4$. After evaporation of the solvent, the crude product (0.68 g in the form of an oil) was purified by flash chromatography over silica gel (eluent:cyclohexane/ethyl acetate 2:8) to afford 30 mg (4.0% of theory) of 3-difluoromethyl-1-methyl-1H-pyrazol-4-yl)-[(S)-2-(2,4,6-trichloro-phenoxymethyl)-pyrrolidin-1-yl]-methanone as a colorless oil.

Example P3

Preparation of 3,5-dichloro-4-[(S)-1-(3-difluoromethyl-1-methyl-1H-pyrazole-4-carbonyl)-pyrrolidin-2-ylmethoxy]-benzaldehyde O-methyl-oxime (compound 1.021)

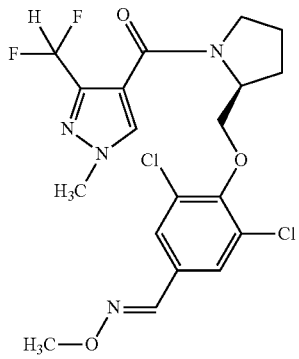 [SMILES: CO/N=C/c1cc(Cl)c(OC[C@@H]2CCCN2C(=O)c2cn(C)nc2C(F)F)c(Cl)c1]

At a temperature of 0° C., a solution of 3-difluoromethyl-1-methyl-1H-pyrazole-4-carbonyl chloride (0.103 g; 0.53 mmol) in dichloromethane (4 ml) was added dropwise to a stirred solution of 3,5-dichloro-4-[(S)-1-pyrrolidin-2-ylmethoxy)-benzaldehyde O-methyl-oxime (0.16 g; 0.53 mmol), which was prepared in analogy as described for example P12, and triethylamine (146 µl; 1.05 mmol) in dichloromethane (7 ml). The ice bath was removed and reaction mixture was allowed stirring for 4 hours. The reaction mixture was washed with 2M HCl (10 ml), 1M NaOH (10 ml) and saturated NaCl (30 ml) and then dried over $Na_2SO_4$. After removal of the solvent, the residue (0.20 g in the form of an oil) was purified by flash chromatography over silica gel (eluent:cyclohexane/ethyl acetate 1:1). 0.14 g (57% of theory) of 3,5-dichloro-4-[(S)-1-(3-difluoromethyl-1-methyl-1H-pyrazole-4-carbonyl)-pyrrolidin-2-ylmethoxy]-benzaldehyde O-methyl-oxime was obtained in form of an oil. $^1$H NMR (400 MHz, $CDCl_3$): δ 1.95 (m, 1H), 2.20 (m, 2H), 2.45 (m, 1H), 3.68 (m, 2H), 3.96 (s, 3H, $NCH_3$), 3.98 (s, 3H, $OCH_3$), 4.22-4.24 (m, 1H), 4.38 (m, 1H), 4.61 (m, 1H), 7.01-7.28 (t, 1H, $CHF_2$), 7.50 (s, 2H, Ar—H), 7.61 (s, 1H), 7.89 (s, 1H). MS $[M+H]^+$ 361/363/365.

Example P4

Preparation of [2-(2,6-dichloro-benzyl)-pyrrolidin-1-yl]-(3-difluoromethyl-1-methyl-1H-pyrazol-4-yl)-methanone (compound 1.110)

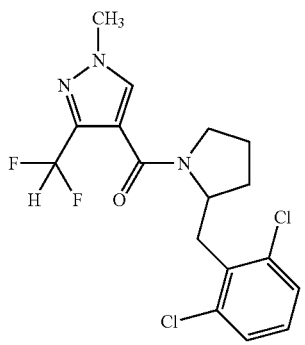 [SMILES: Cn1cc(C(=O)N2CCCC2Cc2c(Cl)cccc2Cl)c(C(F)F)n1]

At a temperature of 0° C., a solution of 3-difluoromethyl-1-methyl-1H-pyrazole-4-carbonyl chloride (0.97 g; 5.0 mmol) in dichloromethane (5 ml) was added dropwise to a stirred suspension of 2-(2,6-dichloro-benzyl)-pyrrolidine (1.20 g; 5.0 mmol), which was prepared as described in example P17, and triethylamine (1.5 g; 15.0 mmol) in dichloromethane (15 ml). The ice bath was removed and reaction mixture was allowed stirring for 15 hours. The reaction mixture was washed with 2M NaOH (20 ml), 2M HCl (20 ml) and saturated NaCl (20 ml) and then dried over $Na_2SO_4$. After removal of the solvent, the residue (1.9 g oil) was purified by flash chromatography over silica gel (eluent:cyclohexane/ethyl acetate 3:7). 1.53 g (78.8% of theory) of [2-(2,6-dichloro-benzyl)-pyrrolidin-1-yl]-(3-difluoromethyl-1-methyl-1H-pyrazol-4-yl)-methanone was obtained in form of an oil.

$^1$H NMR (400 MHz, $CDCl_3$): δ 1.74-2.29 (m, 4H), 2.94-3.80 (m, 4H), 3.85+3.97 (s, 3H, $NCH_3$), 4.5+4.95 (2m, 1H), 6.60-7.77 (m, 5H, $CHF_2$+Ar—H). MS $[M+H]^+$ 388/390/392.

Example P5

Preparation of (4-chloro-phenyl)-[(S)-1-(3-difluoromethyl-1-methyl-1H-pyrazole-4-carbonyl)-pyrrolidin-2-yl]-methanone (compound 1.259)

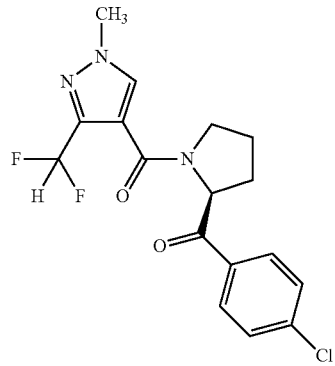 [SMILES: Cn1cc(C(=O)N2CCC[C@H]2C(=O)c2ccc(Cl)cc2)c(C(F)F)n1]

At a temperature of 0° C., a solution of 3-difluoromethyl-1-methyl-1H-pyrazole-4-carbonyl chloride (1.94 g; 10.0 mmol) in dichloromethane (5 ml) was added dropwise to a stirred suspension of (4-chloro-phenyl)-(S)-pyrrolidin-2-yl-methanone hydrochloride (2.46 g; 10.0 mmol), which was prepared as described in example P16, and triethylamine (3.0 g; 30.0 mmol) in dichloromethane (25 ml). Dichloromethane (40 ml) was added to the mixture. The ice bath was removed and reaction mixture was allowed stirring for 3 hours. The reaction mixture was washed with 1M NaOH (20 ml), 1M HCl (20 ml) and saturated NaCl (20 ml) and then dried over $Na_2SO_4$. After removal of the solvent, the residue was purified by flash chromatography over silica gel (eluent:cyclohexane/ethyl acetate 1:19). 3.58 g (97.3% of theory) of (4-chloro-phenyl)-[(S)-1-(3-difluoromethyl-1-methyl-1H-pyrazole-4-carbonyl)-pyrrolidin-2-yl]-methanone was obtained in form of an oil. $^1$H NMR (400 MHz, $CDCl_3$): δ 1.91-1.98 (m, 1H), 2.02-2.16 (m, 2H), 2.33-2.42 (m, 1H), 3.75-3.85 (m, 2H), 3.97 (s, 3H, $NCH_3$), 5.61-5.65 (m, 1H), 6.99-7.28 (t, 1H, $CHF_2$), 7.45-7.47 (d, 2H, Ar—H), 7.73 (s, 1H) 7.96-7.98 (d, 2H, Ar—H). MS $[M+H]^+$ 368/370.

Example P6

Preparation of ((S)-2-{(4-chloro-phenyl)-[(E)-methoxyimino]-methyl}-pyrrolidin-1-yl)-(3-difluoromethyl-1-methyl-1H-pyrazole-4-yl]-methanone (compound 1.281)

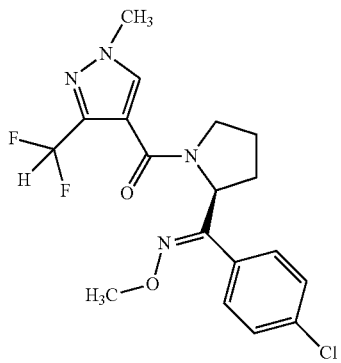 [SMILES: CO/N=C(\c1ccc(Cl)cc1)[C@@H]1CCCN1C(=O)c1cn(C)nc1C(F)F]

To a solution of (4-chloro-phenyl)-[(S)-1-(3-difluoromethyl-1-methyl-1H-pyrazole-4-carbonyl)-pyrrolidin-2-yl]-methanone (370 mg; 1.0 mmol), which was prepared as described in example P5, in methanol (5 ml) at ambient temperature was added O-methylhydroxylamine hydrochloride (126 mg; 1.5 mmol) and pyridine (113 µl; 1.4 mmol). The reaction mixture was stirred for 1.5 hours and water (30 ml) was added. The mixture was extracted with ethylacetate (3×20 ml) and washed with 1N HCl (20 ml). The organic layer was dried over $Na_2SO_4$, filtered, concentrated and dried in vacuo to give 0.390 g oil.

The residue was purified by flash chromatography over silica gel (eluent:cyclohexane/ethyl acetate 1:9). 245 mg (61.7% of theory) of ((S)-2-{(4-chloro-phenyl)-[(E)-methoxyimino]-methyl}-pyrrolidin-1-yl)-(3-difluoromethyl-1-methyl-1H-pyrazole-4-yl]-methanone was obtained in form of an oil.

$^1$H NMR (400 MHz, $CDCl_3$): δ 1.68-1.73 (m, 1H), 1.73-1.79 (m, 1H), 1.98-2.13 (m, 2H), 3.63-3.71 (m, 2H), 3.97 (s, 3H, $NCH_3$), 4.03 (s, 3H, $OCH_3$), 4.48-4.59 (2m, 1H), 6.13-6.28 (d, 1H), 6.96-7.23 (t, 1H, $CHF_2$), 7.36 (d×d, 4H, Ar—H), 7.68 (s, 1H). MS [M+H]$^+$ 397/399.

Example P7

Preparation of {(S)-2-[(4-chlorophenyl)-hydroxy-methyl]-pyrrolidin-1-yl}-(3-difluoromethyl-1-methyl-1H-pyrazol-4-yl)-methanone (compound 1.237)

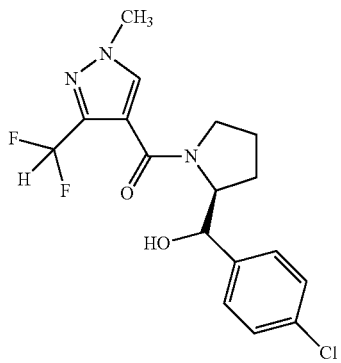 [SMILES: Cn1cc(C(=O)N2CCC[C@H]2C(O)c2ccc(Cl)cc2)c(C(F)F)n1]

To a solution of (4-chloro-phenyl)-[(S)-1-(3-difluoromethyl-1-methyl-1H-pyrazole-4-carbonyl)-pyrrolidin-2-yl]-methanone (370 mg; 1.0 mmol), which was prepared as described in example P5, in methanol (5 ml) at 0° C. was added portionwise sodium borohydride (35 mg; 1.0 mmol). The reaction mixture was stirred for 0.5 hours and 1N HCl was added until pH 7 reached. Solvent was removed under pressure and the remaining mixture was extracted with ethylacetate (2×20 ml). The combined organic layer was dried over $Na_2SO_4$, filtered, concentrated and dried in vacuo to give 0.31 g (83.3% of theory) of {(S)-2-[(4-chlorophenyl)-hydroxy-methyl]-pyrrolidin-1-yl}-(3-difluoromethyl-1-methyl-1H-pyrazol-4-yl)-methanone as an oil.

$^1$H NMR (400 MHz, $CDCl_3$): δ 1.51-1.58 (m, 1H), 1.61-1.73 (m, 1H), 1.74-1.84 (m, 2H), 3.49-3.55 (m, 1H), 3.65-3.73 (m, 1H), 3.97 (s, 3H, $NCH_3$), 4.53-4.69 (q, 1H), 4.62-4.69 (d, 1H), 5.82 ($s_{broad}$, 1H), 6.96-7.23 (t, 1H, $CHF_2$), 7.33 (d×d, 4H, Ar—H), 7.64 (s, 1H). MS [M+H]$^+$ 370/372.

Example P8

Preparation of {(S)-2-[(4-chlorophenyl)-fluoro-methyl]-pyrrolidin-1-yl}-(3-difluoromethyl-1-methyl-1H-pyrazol-4-yl)-methanone (compound 1.215)

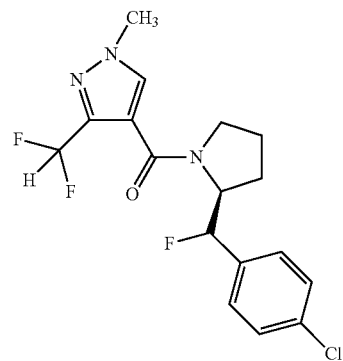 [SMILES: Cn1cc(C(=O)N2CCC[C@H]2C(F)c2ccc(Cl)cc2)c(C(F)F)n1]

To a solution of {(S)-2-[(4-chlorophenyl)-hydroxy-methyl]-pyrrolidin-1-yl}-(3-difluoromethyl-1-methyl-1H-pyrazol-4-yl)-methanone (370 mg; 1.0 mmol), which was prepared as described in example P7, in dichloromethane (4 ml) at 0° C. was added dropwise DAST (0.15 ml; 1.1 mmol) in dichloromethane (1 ml). The reaction mixture was stirred for 15 hours and water (30 ml) was added. The mixture was extracted with ethylacetate (2×20 ml), washed with 1N HCl (30 ml), NaHCO3 satd. (20 ml), water (20 ml). The organic layer was dried over Na2SO4, filtered, concentrated and dried in vacuo to give 0.290 g of a brown oil.

The residue was purified twice by flash chromatography over silica gel (eluent:cyclohexane/ethyl acetate 1:19). 45 mg (12.1% of theory) of {(S)-2-[(4-chlorophenyl)-fluoro-methyl]-pyrrolidin-1-yl}-(3-difluoromethyl-1-methyl-1H-pyrazol-4-yl)-methanone was obtained in form of an oil. $^1$H NMR (400 MHz, $CDCl_3$): δ 1.68-1.73 (m, 1H), 1.73-1.79 (m, 1H), 1.98-2.13 (m, 2H), 3.63-3.71 (m, 2H), 3.97 (s, 3H, $NCH_3$), 4.48-4.59 (2m, 1H), 6.13-6.28 (d, 1H), 6.96-7.23 (t, 1H, $CHF_2$), 7.36 (d×d, 4H, Ar—H), 7.68 (s, 1H). MS [M+H]$^+$ 372/374.

Example P8

Preparation of (3-difluoromethyl-1-methyl-1H-pyrazol-4-yl)-((S)-(2-hydroxymethyl-pyrrolidin-1-yl)-methanone

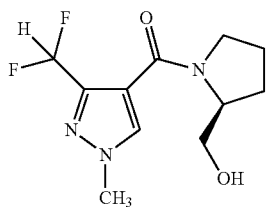 [SMILES: Cn1cc(C(=O)N2CCC[C@H]2CO)c(C(F)F)n1]

At a temperature of 0° C., a solution of 3-difluoromethyl-1-methyl-1H-pyrazole-4-carbonyl chloride (1.9 g, 10.0 mol) in dichloromethane (40 ml) was added dropwise to a stirred solution of (S)-pyrrolidin-2-yl-methanol (1.0 g, 10.0 mmol) and triethylamine (2.8 ml, 20.0 mmol) in dichloromethane 60 ml. The reaction mixture was stirred for 10 minutes at ambient temperature and then allowed to stand for 3 h at ambient temperature. The reaction mixture was washed with 1M NaOH (30 ml) and 2M HCl (30 ml) and then dried over Na$_2$SO$_4$. After removal of the solvent, the residue (1.76 g in the form of an oil) was purified by flash chromatography over silica gel (eluent:dichloromethane/methanol 9:1). 1.28 g (49% of theory) of (3-difluoromethyl-1-methyl-1H-pyrazol-4-yl)-((S)-(2-hydroxymethyl-pyrrolidin-1-yl)-methanone was obtained in form of an oil.

$^1$H NMR (400 MHz, CDCl$_3$): δ 1.64-1.74 (m, 1H), 1.82-2.04 (m, 2H), 2.01-2.18 (m, 1H), 3.51-3.57 (m, 1H), 3.63-3.70 (m, 2H), 3.75-3.79 (m, 1H), 3.96 (s, 3H, NCH$_3$), 4.37-4.38 (d, 1H), 4.54-4.56 (d, 1H), 6.92-7.20 (t, 1H, CHF$_2$), 7.61 (s, 2H, Ar—H). MS [M+H]$^+$ 260. [α]$^{23}_D$=−69.3 (c 5.8, CHCl$_3$).

Example P9

Preparation of ((S)-2-chloromethyl-pyrrolidin-1-yl)-(3-difluoromethyl-1-methyl-1H-pyrazol-4-yl)-methanone

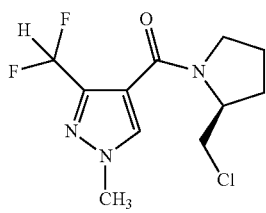 [SMILES: Cn1cc(C(=O)N2CCC[C@H]2CCl)c(C(F)F)n1]

At 0° C., p-toluenesulfonylchloride (0.92 g, 4.8 mol) was added portionwise to a stirred solution of (3-difluoromethyl-1-methyl-1H-pyrazol-4-yl)-((S)-(2-hydroxymethyl-pyrrolidin-1-yl)-methanone (1.0 g, 3.9 mmol), which was prepared as described in example P8, and pyridine (2.35 ml, 29.3 mmol) in dichloromethane (10 ml). The reaction mixture was stirred for 30 minutes at 0° C. and then allowed to stand for 15 hours at ambient temperature. Then dichloromethane (40 ml) was added. The solution was washed with water (4×50 ml) and saturated NaCl (50 ml) and then dried over Na$_2$SO$_4$. After evaporation of the solvent, the crude product (0.88 g in the form of an oil) was purified by flash chromatography over silica gel (eluent:cyclohexane/ethyl acetate 3:7) to afford 0.58 g (36.0% of theory) of ((S)-2-chloromethyl-pyrrolidin-1-yl)-(3-difluoromethyl-1-methyl-1H-pyrazol-4-yl)-methanone as a colorless oil.

$^1$H NMR (400 MHz, CDCl$_3$): δ 1.88-1.93 (m, 1H), 2.03-2.22 (m, 3H), 3.54-3.60 (m, 1H), 3.63-3.68 (m, 1H), 3.77-3.85 (m, 1H), 3.94-3.97 (m, 1H), 4.00 (s, 3H), 4.50 (m, 1H), 6.95-7.22 (t, 1H, CHF$_2$), 7.60 (s, 1H). MS [M+H]$^+$ 278/80. [α]$^{23}_D$=−104.41 (c 5.21, CHCl$_3$).

Example P10

Preparation of (S)-2-(toluene-4-sulfonyloxymethyl)-pyrrolidine-1-carboxylic acid tert-butyl ester

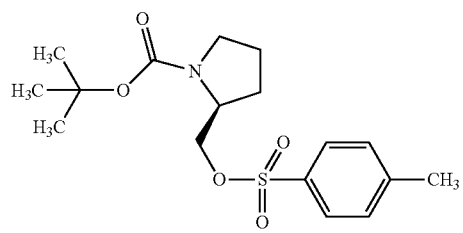 [SMILES: Cc1ccc(S(=O)(=O)OC[C@@H]2CCCN2C(=O)OC(C)(C)C)cc1]

At a temperature of 0° C., p-toluenesulfonylchloride (6.0 g, 30.4 mol) was added portionwise to a stirred solution of (S)-hydroxymethyl-pyrrolidine-1-carboxylic acid tert-butyl ester (4.9 g, 24.3 mmol) and pyridine (14.6 ml, 181 mmol) in dichloromethane (50 ml). The reaction mixture was stirred for 30 minutes at 0° C. and then allowed to stand for 15 hours at ambient temperature. Then dichloromethane (50 ml) was added. The solution was washed with water (4×50 ml) and saturated NaCl (50 ml) and then dried over Na$_2$SO$_4$. After evaporation of the solvent, the crude product (9.83 g in the form of an oil) was purified by flash chromatography over silica gel (eluent:cyclohexane/ethyl acetate 1:1) to afford 8.07 g (83.4% of theory) of (S)-2-(toluene-4-sulfonyloxymethyl)-pyrrolidine-1-carboxylic acid tert-butyl ester as a colorless oil. $^1$H NMR (400 MHz, DMSO): δ 1.29 and 1.35 (s, 9H), 1.72 (m, 3H), 1.92 (m, 1H), 2.43 (s, 3H), 3.18 (m, 2H), 3.83 (m, 1H), 4.03 (m, 2H), 7.49 (d, 2H), 7.78 (d, 2H). MS [M+H]$^+$ 256. [α]$^{23}_D$=−39.1 (c 5.98, CHCl$_3$).

Example P11

Preparation of (S)-2-(2,4,6-trichloro-phenoxymethyl)-pyrrolidine-1-carboxylic acid tert-butyl ester

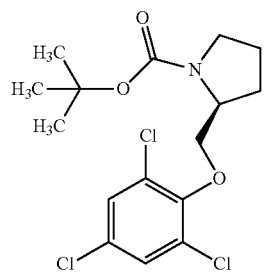 [SMILES: CC(C)(C)OC(=O)N1CCC[C@H]1COc1c(Cl)cc(Cl)cc1Cl]

At a temperature of 0° C. sodium hydride 55% in oil (0.12 g, 2.8 mmol) was added over 10 minutes to a solution of 2,4,6-trichlorophenol (0.55 g, 2.8 mmol) in DMF (10 ml). The reaction mixture was warmed to ambient temperature and stirred 20 minutes, then a solution of (S)-2-(toluene-4-sulfonyloxymethyl)-pyrrolidine-1-carboxylic acid tert-butyl ester (1.0 g, 2.8 mmol), which was prepared as described in example P10, in DMF (5 ml) was added. The reaction mixture was stirred for 15 hours at ambient temperature. The reaction mixture was heated to a temperature of 80° C. and stirred for another 5 hours. After cooling, the reaction mixture was poured on 1N HCl (50 ml) and then extracted with ethyl acetate (2×80 ml). The organic layers was washed with saturated NaCl (50 ml) and then dried over $Na_2SO_4$. After evaporation of the solvent, the crude product (0.81 g in the form of a yellow oil) was purified by flash chromatography over silica gel (eluent:cyclohexane/ethyl acetate 9:1) to afford 0.32 g (29.9% of theory) of (S)-2-(2,4,6-trichloro-phenoxymethyl)-pyrrolidine-1-carboxylic acid tert-butyl ester as a colorless oil. $^1$H NMR (400 MHz, $CDCl_3$): δ 1.48 and 1.52 (s, 9H), 1.72 (m, 2H), 2.12 (m, 1H), 2.43 (m, 1H), 3.41 (m, 2H), 4.13 (m, 3H), 7.30 (s, 2H, Ar—H). MS $[M+H]^+$ 380/382/384. $[α]^{23}_D$=−31.6 (c 4.13, $CHCl_3$).

Example P12

Preparation of (S)-2-(2,4,6-trichloro-phenoxymethyl)-pyrrolidine hydrochloride

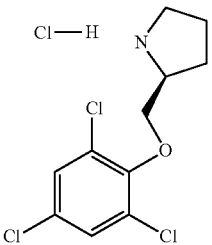

(S)-2-(2,4,6-trichloro-phenoxymethyl)-pyrrolidine-1-carboxylic acid tert-butyl ester (280 mg, 0.73 mmol), which was prepared as described in example P11, was stirred at ambient temperature in 4N HCl in dioxane (2 ml) for 2 hours. After evaporation of the solvent, the residue was stirred with ether (5 ml). The white crystals are filtered off, washed with ether (5 ml) and dried at 30° C. in the vacuum oven. 70 mg (34% of theory) of (S)-2-(2,4,6-trichloro-phenoxymethyl)-pyrrolidine hydrochloride was obtained as a white solid.

$^1$H NMR (400 MHz, DMSO): δ 1.80 (m, 1H), 1.96 (m, 2H), 2.13 (m, 1H), 3.22 (m, 2H), 3.89 (m, 1H), 4.25 (m, 2H), 7.75 (s, 2H). MS $[M+H]^+$ 280/282/284.

Example P13

Preparation of (S)-2-(2,4,6-trichloro-phenoxymethyl)-pyrrolidine

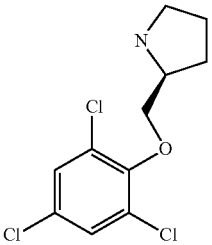 [SMILES: Clc1cc(Cl)c(OC[C@@H]2CCCN2)c(Cl)c1]

Sodium hydride 55% in oil (1.4 g; 29.8 mmol) was added portionwise over 10 minutes to a stirred solution of 2,4,6-trichlorophenol (5.89 g; 29.8 mmol) in dry dimethylformamide (90 ml) at a temperature of 10° C. under nitrogen. The reaction mixture was stirred for 20 minutes at ambient temperature followed by the addition of (S)-tetrahydro-pyrrolo[1,2-c][1,2,3]oxathiazole 1,1-dioxide (5.0 g; 30.6 mmol), which was prepared as described in example P14, in dimethylformamide (25 ml). The reaction mixture was stirred for 4 hours at ambient temperature then poured onto 1M HCl (400 ml) and extracted with ethyl acetate (2×200 ml). The combined ethyl acetate layers are washed with water (2×100 ml), saturated NaCl (100 ml) and then dried over $Na_2SO_4$. After removal of the solvent the residue (11.1 g oil) was dissolved in dioxane (150 ml) and treated with sulphuric acid (2.9 ml) and water (2.9 ml). The reaction mixture was stirred at ambient temperature for 15 hours. The reaction mixture was poured on sat. $NaHCO_3$ (300 ml) and extracted with dichloromethane (3×200 ml). The organic layers are washed with saturated NaCl (100 ml) and then dried over $Na_2SO_4$. After evaporation of the solvent, the crude product (7.16 g in the form of a orange oil) was purified by flash chromatography over silica gel (eluent:dichloromethane/methanol 9:1) to afford 3.53 g (42.0% of theory) of (S)-2-(2,4,6-trichloro-phenoxymethyl)-pyrrolidine as a oil.

$^1$H NMR (400 MHz, $CDCl_3$): δ 1.79-1.87 (m, 1H), 2.01-2.14 (m, 2H), 2.16-2.22 (m, 1H), 3.21-3.26 (m, 1H), 3.39-3.51 (m, 1H), 3.92-4.01 (m, 1H), 4.18-4.24 (m, 2H), 4.75 ($m_{broad}$, 1H, NH) 7.28 (s, 2H, Ar—H). MS $[M+H]^+$ 280/282/284. $[α]^{24}_D$=−20.4 (c 4.5, $CHCl_3$).

Example P14

Preparation of (S)-tetrahydro-pyrrolo[1,2-c][1,2,3]oxathiazole 1,1-dioxide

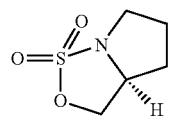

To a solution of (S)-pyrrolidin-2-yl-methanol (25.0 g, 0.247 mol) in dichloromethane (165 ml) was added pyridine (41 ml, 0.508 mol). The solution was stirred while being cooled in dry ice/acetone bath until the temperature of the mixture was below −68° C. Sulfuryl chloride (20 ml, 0.247 mol) was added over 45 minutes while maintaining the reaction temperature below −60° C. The reaction temperature was allowed to warm to −40° C. and held for two hours while pyridine hydrochloride precipitates. The reaction mixture was allowed to warm to ambient temperature and was stirred for an additional 50 minutes. The reaction mixture was poured onto ice water (300 ml). The organic layer was separated and the aqueous phase was extracted with dichloromethane (150 ml). The combined organic layers are washed with 1N HCl (100 ml), water (100 ml) and saturated NaCl (100 ml) and then dried over $Na_2SO_4$. After evaporation of the solvent, the crude product (32.4 g in the form of a orange resin) was purified by flash chromatography over silica gel (eluent:cyclohexane/ethyl acetate 6:4) to afford 29.3 g (72.7% of theory) of (S)-tetrahydro-pyrrolo[1,2-c][1,2,3]oxathiazole 1,1-dioxide as a white solid m.p. 46-50° C.

$^1$H NMR (400 MHz, $CDCl_3$): δ 1.78-1.87 (m, 1H), 1.92-2.00 (m, 2H), 2.17-2.22 (m, 1H), 3.23-3.30 (m, 1H), 3.65-

3.73 (m, 1H), 4.03-4.09 (m, 1H), 4.24-4.31 (m, 1H), 4.54-4.59 (m, 1H). MS [M+H]+ 164. [α]23D=+42.0 (c 5.34, CHCl3).

Example P15

Preparation of (S)-2-(4-chloro-benzoyl)-pyrrolidine-1-carboxylic acid tert-butyl ester

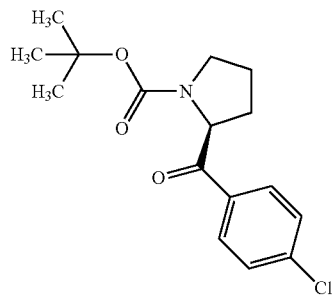 [SMILES: CC(C)(C)OC(=O)N1CCC[C@H]1C(=O)c1ccc(Cl)cc1]

At 0° C. 4-chlorophenylmagnesiumbromide 0.9 molar in THF/toluene (66.7 ml, 60 mmol) was added over 15 minutes to a solution of (S)-2-(Methoxy-methyl-carbamoyl)-pyrrolidine-1-carboxylic acid tert-butyl ester CAS 115186-37-3 (5.16 g, 20 mmol) in dry THF (50 ml). The reaction mixture was warmed to ambient temperature and stirred for another 4 hours. The reaction mixture was poured on 1N HCl/ice (150 ml) and then extracted with ethyl acetate (2×100 ml). The organic layers are washed with water (2×50 ml), saturated NaCl (50 ml) and then dried over Na2SO4. After evaporation of the solvent, the crude product (7.5 g in the form of a yellow oil) was purified by flash chromatography over silica gel 150 g, (eluent:cyclohexane/ethyl acetate 9:1) to afford 4.3 g (69.4% of theory) of (S)-2-(4-chloro-benzoyl)-pyrrolidine-1-carboxylic acid tert-butyl ester as a as a white solid m.p. 117-122° C.

1H NMR (400 MHz, CDCl3): δ 1.26 (m, 9H), 1.86-1.98 (m, 3H), 2.23-2.37 (m, 1H), 3.45-3.69 (m, 2H), 5.13-5.37 (m, 1H), 7.46 (d, 2H, Ar—H), 7.91 (d, 2H, Ar—H). MS [M+H]+ 380/382/384.

Example P16

Preparation of (4-chloro-phenyl)-(S)-pyrrolidin-2-yl-methanone hydrochloride

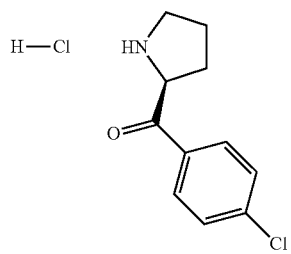 [SMILES: Cl ; O=C(c1ccc(Cl)cc1)[C@@H]1CCCN1]

At 0° C. (S)-2-(4-chloro-benzoyl)-pyrrolidine-1-carboxylic acid tert-butyl ester (4.2 g, 13.5 mmol), which was prepared as described in example P15, was added in one portion to a 4M HCl in dioxane (10 ml, 40 mmol), while stirring for two hours. After removal of the solvent, the residue was filtered off and washed with ether (10 ml) and dryed, to afford 2.58 g (77.3% of theory) of (4-chloro-phenyl)-(S)-pyrrolidin-2-yl-methanone hydrochloride as a white solid m.p. 176-179° C.

1H NMR (400 MHz, DMSO): δ 1.78-1.91 (m, 2H), 1.93-2.04 (m, 1H), 2.47-2.52 (m, 1H), 3.24-3.27 (m, 2H), 5.32-5.39 (m, 1H), 7.68 (d, 2H, Ar—H), 8.11 (d, 2H, Ar—H).

Example P17

Preparation of 2-(2,6-dichloro-benzyl)-pyrrolidine

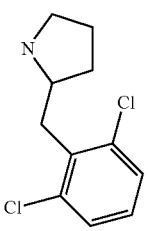 [SMILES: Clc1cccc(Cl)c1CC1CCCN1]

To a solution of 5-(4-chloro-benzyl)-3,4-dihydro-2H-pyrrole (1.14 g; 5.0 mmol), which was prepared as described in example P18, in methanol (20 ml) at 0° C. was added portionwise sodium borohydride (0.38 g; 10 mmol). The reaction mixture was stirred for 1.5 hours at ambient temperature and ice-water (100 ml) was added. The reaction mixture was extracted with dichloromethane (3×40 ml), washed with 1M NaOH and then dried over Na2SO4. After removal of the solvent 1.15 g (100% of theory) of 2-(2,6-dichloro-benzyl)-pyrrolidine was obtained in form of a liquid. MS [M+H]+ 230/232/234.

Example P18

Preparation of 5-(2,6-dichloro-benzyl)-3,4-dihydro-2H-pyrrole

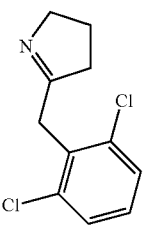 [SMILES: Clc1cccc(Cl)c1CC1=NCCC1]

To a mixture of water (45 ml) and HCl conc. (45 ml) at reflux temperature was added dropwise during 15 minutes a solution of 3-[2-(2,6-dichloro-phenyl)-acetyl]-1-vinyl-pyrrolidin-2-one (2.98 g; 10 mmol), which was prepared as described in example P19, in THF (25 ml). The solution was concentrated to dryness on a rotary evaporator. The residue was dissolved in dichloromethane (20 ml), washed with water (2×30 ml) and dried over Na2SO4 and filtered through silica-gel (5 g). After removal of the solvent 2.60 g (>100% of theory) of 5-(2,6-dichloro-benzyl)-3,4-dihydro-2H-pyrrole was obtained in form of a brown liquid.

¹H NMR (400 MHz, CDCl₃): δ 1.85-1.89 (m, 2H), 2.48-2.53 (t, 2H), 3.55+3.73 (m, 2H), 4.00 (s, 2H), 7.10-7.17 (d×d, 1H, Ar—H), 7.28-7.31 (d, 2H, Ar—H). MS [M+H]⁺ 228/230/232.

Example P19

Preparation of 3-[2-(2,6-dichloro-phenyl)-acetyl]-1-vinyl-pyrrolidin-2-one

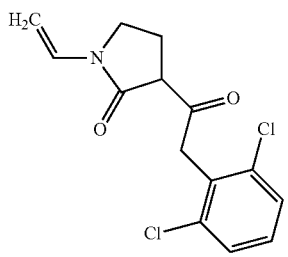 [SMILES: C=CN1CCC(C(=O)Cc2c(Cl)cccc2Cl)C1=O]

A mixture of N-vinylpyrrolidinone (2.78 g; 25 mmol) and (2,6-dichloro-phenyl)-acetic acid ethylester (6.41 g; 27.5 mmol) in THF (4 ml) was dropped slowly to a 60% NaH suspension (3.0 g; 70 mmol) in THF (14 ml) while stirring at 50° C. for 30' under nitrogen stream. The mixture was stirred at 62° C. for another 1.5 hours.

The mixture was cooled to ambient temperature and poured carefully onto ammoniumchloride satd. (80 ml). The mixture was extracted with ethylacetate (70 ml) and washed with water (20 ml). The organic layer was dried over Na₂SO₄, filtered, concentrated and dried in vacuo to give 7.0 g of an oil. The residue was purified by flash chromatography over silica gel (eluent:cyclohexane/ethyl acetate 9:1). 4.3 g (57.7% of theory) of 3-[2-(2,6-dichloro-phenyl)-acetyl]-1-vinyl-pyrrolidin-2-one was obtained in form of a white solid m.p. 101-108° C.

¹H NMR (400 MHz, CDCl₃): δ 2.15-2.24 (m, 1H), 2.67-2.74 (m, 1H), 3.47-3.62 (m, 2H), 3.85-3.89 (m, 1H), 4.25-4.30 (d, 1H), 4.45-4.54 (m, 2H), 4.74-4.78 (d, 1H), 7.07-7.11 (m, 1H), 7.14-7.18 (d×d, 1H, Ar—H), 7.31-7.34 (d, 2H, Ar—H). MS [M+H]⁺ 298/300/302.

Example P20

Preparation of (2-chloro-pyridin-3-yl)-[(S)-2-(2,4,6-trichloro-phenoxymethyl)-pyrrolidin-1-yl]-methanone (compound 2.006)

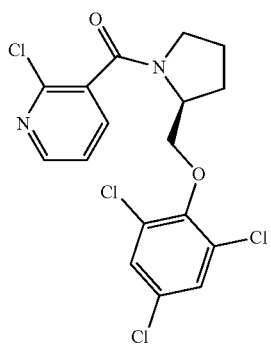 [SMILES: O=C(c1cccnc1Cl)N1CCC[C@H]1COc1c(Cl)cc(Cl)cc1Cl]

At a temperature of 0° C., a solution of 2-chloro-nicotinoyl chloride (0.313 g; 1.78 mmol) in dichloromethane (5 ml) was added dropwise to a stirred solution of (S)-2-(2,4,6-trichloro-phenoxymethyl)-pyrrolidine (0.30 g; 1.78 mmol), which was prepared as described in example P13, and triethylamine (0.50 ml; 3.56 mmol) in dichloromethane (10 ml). The ice bath was removed and reaction mixture was allowed stirring for 16 hours at ambient temperature. Dichloromethane (40 ml) was added to the mixture. The reaction mixture was washed with 2M HCl (40 ml), 1M NaOH (50 ml) and saturated NaCl (50 ml) and then dried over Na₂SO₄. After removal of the solvent, the residue (0.21 g in the form of an oil) was purified by flash chromatography over silica gel (eluent:cyclohexane/ethyl acetate 1:1). 0.134 g (17.9% of theory) of (2-chloro-pyridin-3-yl)-[(S)-2-(2,4,6-trichloro-phenoxymethyl)-pyrrolidin-1-yl]-methanone was obtained in form of an oil. ¹H NMR (400 MHz, CDCl₃): δ 1.88-1.97 (m, 1H), 2.10-2.28 (m, 2H), 2.47-2.54 (m, 1H), 3.30-3.41 (m, 2H), 4.21-4.24 (m, 1H), 4.44 (m, 1H), 4.60-4.65 (m, 1H), 7.26 (s, 2H, Ar—H), 7.30-7.34 (m, 1H, Py-H), 7.68-7.72 (m, 1H, Py-H), 8.42-8.44 (m, 1H, Py-H). MS [M+H]⁺ 419/421/423/425.

Table 1: Compounds of Formula Ia:

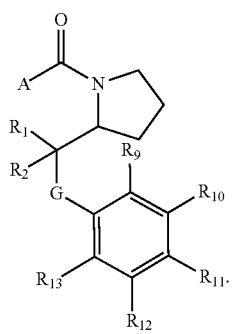

(Ia)

wherein A is the group A₁,

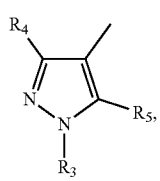

(A₁)

wherein R₃ is methyl, R₄ is difluoromethyl and R₅ is hydrogen.

"Me" is methyl, "Et" is ethyl, "n-Pr" is n-propyl, "i-Pr" is isopropyl, "c-Pr" is cyclopropyl, "c-Bu" is cyclobutyl, "n-Bu" is n-butyl, "i-Bu" is isobutyl, "t-Bu" is tertiary butyl and "n-Hex" is n-hexyl.

TABLE 1

| Cpd No. | R₁ | R₂ | G | R₉ | R₁₀ | R₁₁ | R₁₂ | R₁₃ |
|---|---|---|---|---|---|---|---|---|
| 1.001 | H | H | O | Cl | H | H | H | H |
| 1.002 | H | H | O | H | H | Cl | H | H |
| 1.003 | H | H | O | Cl | H | Cl | H | H |
| 1.004 | H | H | O | Cl | H | H | H | Cl |
| 1.005 | H | H | O | Cl | Cl | H | H | Cl |
| 1.006 | H | H | O | Cl | H | Cl | H | Cl |
| 1.007 | H | H | O | Cl | H | Br | H | Cl |

TABLE 1-continued

| Cpd No. | R₁ | R₂ | G | R₉ | R₁₀ | R₁₁ | R₁₂ | R₁₃ |
|---|---|---|---|---|---|---|---|---|
| 1.008 | H | H | O | Cl | H | I | H | Cl |
| 1.009 | H | H | O | Cl | H | CHF₂ | H | Cl |
| 1.010 | H | H | O | Cl | H | CF₃ | H | Cl |
| 1.011 | H | H | O | Cl | H | Me | H | Cl |
| 1.012 | H | H | O | Cl | H | Et | H | Cl |
| 1.013 | H | H | O | Cl | H | n-Pr | H | Cl |
| 1.014 | H | H | O | Cl | H | i-Pr | H | Cl |
| 1.015 | H | H | O | Cl | H | c-Pr | H | Cl |
| 1.016 | H | H | O | Cl | H | n-Bu | H | Cl |
| 1.017 | H | H | O | Cl | H | i-Bu | H | Cl |
| 1.018 | H | H | O | Cl | H | c-Bu | H | Cl |
| 1.019 | H | H | O | Cl | H | t-Bu | H | Cl |
| 1.020 | H | H | O | Cl | H | n-Hex | H | Cl |
| 1.021 | H | H | O | Cl | H | CH=NOMe | H | Cl |
| 1.022 | H | H | O | Cl | H | CH=NOEt | H | Cl |
| 1.023 | H | H | O | Cl | H | CH=NO—n-Pr | H | Cl |
| 1.024 | H | H | O | Cl | H | C(Me)=NOMe | H | Cl |
| 1.025 | H | H | O | Cl | H | C(Me)=NOEt | H | Cl |
| 1.026 | H | H | O | Cl | H | H | H | Me |
| 1.027 | H | H | O | Cl | H | Cl | H | Me |
| 1.028 | H | H | O | Cl | H | Br | H | Me |
| 1.029 | H | H | O | Cl | H | I | H | Me |
| 1.030 | H | H | O | Cl | H | CHF₂ | H | Me |
| 1.031 | H | H | O | Cl | H | CF₃ | H | Me |
| 1.032 | H | H | O | Cl | H | Me | H | Me |
| 1.033 | H | H | O | Cl | H | Et | H | Me |
| 1.034 | H | H | O | Cl | H | n-Pr | H | Me |
| 1.035 | H | H | O | Cl | H | i-Pr | H | Me |
| 1.036 | H | H | O | Cl | H | c-Pr | H | Me |
| 1.037 | H | H | O | Cl | H | n-Bu | H | Me |
| 1.038 | H | H | O | Cl | H | i-Bu | H | Me |
| 1.039 | H | H | O | Cl | H | c-Bu | H | Me |
| 1.040 | H | H | O | Cl | H | t-Bu | H | Me |
| 1.041 | H | H | O | Cl | H | n-Hex | H | Me |
| 1.042 | H | H | O | Cl | H | CH=NOMe | H | Me |
| 1.043 | H | H | O | Cl | H | CH=NOEt | H | Me |
| 1.044 | H | H | O | Cl | H | CH=NO—n-Pr | H | Me |
| 1.045 | H | H | O | Cl | H | C(Me)=NOMe | H | Me |
| 1.046 | H | H | O | Cl | H | C(Me)=NOEt | H | Me |
| 1.047 | H | H | O | Br | H | H | H | Br |
| 1.048 | H | H | O | Br | H | Cl | H | Br |
| 1.049 | H | H | O | Br | H | Br | H | Br |
| 1.050 | H | H | O | Br | H | I | H | Br |
| 1.051 | H | H | O | Br | H | CHF₂ | H | Br |
| 1.052 | H | H | O | Br | H | CF₃ | H | Br |
| 1.053 | H | H | O | Br | H | Me | H | Br |
| 1.054 | H | H | O | Br | H | Et | H | Br |
| 1.055 | H | H | O | Br | H | n-Pr | H | Br |
| 1.056 | H | H | O | Br | H | i-Pr | H | Br |
| 1.057 | H | H | O | Br | H | c-Pr | H | Br |
| 1.058 | H | H | O | Br | H | n-Bu | H | Br |
| 1.059 | H | H | O | Br | H | i-Bu | H | Br |
| 1.060 | H | H | O | Br | H | c-Bu | H | Br |
| 1.061 | H | H | O | Br | H | t-Bu | H | Br |
| 1.062 | H | H | O | Br | H | n-Hex | H | Br |
| 1.063 | H | H | O | Br | H | CH=NOMe | H | Br |
| 1.064 | H | H | O | Br | H | CH=NOEt | H | Br |
| 1.065 | H | H | O | Br | H | CH=NO—n-Pr | H | Br |
| 1.066 | H | H | O | Br | H | C(Me)=NOMe | H | Br |
| 1.067 | H | H | O | Br | H | C(Me)=NOEt | H | Br |
| 1.068 | H | H | O | Me | H | H | H | Me |
| 1.069 | H | H | O | Me | H | Cl | H | Me |
| 1.070 | H | H | O | Me | H | Br | H | Me |
| 1.071 | H | H | O | Me | H | I | H | Me |
| 1.072 | H | H | O | Me | H | CHF₂ | H | Me |
| 1.073 | H | H | O | Me | H | CF₃ | H | Me |
| 1.074 | H | H | O | Me | H | Me | H | Me |
| 1.075 | H | H | O | Me | H | Et | H | Me |
| 1.076 | H | H | O | Me | H | n-Pr | H | Me |
| 1.077 | H | H | O | Me | H | i-Pr | H | Me |
| 1.078 | H | H | O | Me | H | c-Pr | H | Me |
| 1.079 | H | H | O | Me | H | n-Bu | H | Me |
| 1.080 | H | H | O | Me | H | i-Bu | H | Me |
| 1.081 | H | H | O | Me | H | c-Bu | H | Me |
| 1.082 | H | H | O | Me | H | t-Bu | H | Me |
| 1.083 | H | H | O | Me | H | n-Hex | H | Me |
| 1.084 | H | H | O | Me | H | CH=NOMe | H | Me |
| 1.085 | H | H | O | Me | H | CH=NOEt | H | Me |
| 1.086 | H | H | O | Me | H | CH=NO—n-Pr | H | Me |
| 1.087 | H | H | O | Me | H | C(Me)=NOMe | H | Me |
| 1.088 | H | H | O | Me | H | C(Me)=NOEt | H | Me |
| 1.089 | H | H | O | Cl | H | H | H | H |
| 1.090 | H | H | O | Cl | H | Cl | H | H |
| 1.091 | H | H | O | Cl | H | Br | H | H |
| 1.092 | H | H | O | Cl | H | I | H | H |
| 1.093 | H | H | O | Cl | H | CHF₂ | H | H |
| 1.094 | H | H | O | Cl | H | CF₃ | H | H |
| 1.095 | H | H | O | Cl | H | Me | H | H |
| 1.096 | H | H | O | Cl | H | Et | H | H |
| 1.097 | H | H | O | Cl | H | n-Pr | H | H |
| 1.098 | H | H | O | Cl | H | i-Pr | H | H |
| 1.099 | H | H | O | Cl | H | c-Pr | H | H |
| 1.100 | H | H | O | Cl | H | n-Bu | H | H |
| 1.101 | H | H | O | Cl | H | i-Bu | H | H |
| 1.102 | H | H | O | Cl | H | c-Bu | H | H |
| 1.103 | H | H | O | Cl | H | t-Bu | H | H |
| 1.104 | H | H | O | Cl | H | n-Hex | H | H |
| 1.105 | H | H | O | Cl | H | CH=NOMe | H | H |
| 1.106 | H | H | O | Cl | H | CH=NOEt | H | H |
| 1.107 | H | H | O | Cl | H | CH=NO—n-Pr | H | H |
| 1.108 | H | H | O | Cl | H | C(Me)=NOMe | H | H |
| 1.109 | H | H | O | Cl | H | C(Me)=NOEt | H | H |
| 1.110 | H | H | bond | Cl | H | H | H | Cl |
| 1.111 | H | H | bond | Cl | H | Cl | H | Cl |
| 1.112 | H | H | bond | Cl | H | Br | H | Cl |
| 1.113 | H | H | bond | Cl | H | I | H | Cl |
| 1.114 | H | H | bond | Cl | H | CHF₂ | H | Cl |
| 1.115 | H | H | bond | Cl | H | CF₃ | H | Cl |
| 1.116 | H | H | bond | Cl | H | Me | H | Cl |
| 1.117 | H | H | bond | Cl | H | Et | H | Cl |
| 1.118 | H | H | bond | Cl | H | n-Pr | H | Cl |
| 1.119 | H | H | bond | Cl | H | i-Pr | H | Cl |
| 1.120 | H | H | bond | Cl | H | c-Pr | H | Cl |
| 1.121 | H | H | bond | Cl | H | n-Bu | H | Cl |
| 1.122 | H | H | bond | Cl | H | i-Bu | H | Cl |
| 1.123 | H | H | bond | Cl | H | c-Bu | H | Cl |
| 1.124 | H | H | bond | Cl | H | t-Bu | H | Cl |
| 1.125 | H | H | bond | Cl | H | n-Hex | H | Cl |
| 1.126 | H | H | bond | Cl | H | CH=NOMe | H | Cl |
| 1.127 | H | H | bond | Cl | H | CH=NOEt | H | Cl |
| 1.128 | H | H | bond | Cl | H | CH=NO—n-Pr | H | Cl |
| 1.129 | H | H | bond | Cl | H | C(Me)=NOMe | H | Cl |
| 1.130 | H | H | bond | Cl | H | C(Me)=NOEt | H | Cl |
| 1.131 | H | H | bond | Cl | H | H | H | Me |
| 1.132 | H | H | bond | Cl | H | Cl | H | Me |
| 1.133 | H | H | bond | Cl | H | Br | H | Me |
| 1.134 | H | H | bond | Cl | H | I | H | Me |
| 1.135 | H | H | bond | Cl | H | CHF₂ | H | Me |
| 1.136 | H | H | bond | Cl | H | CF₃ | H | Me |
| 1.137 | H | H | bond | Cl | H | Me | H | Me |
| 1.138 | H | H | bond | Cl | H | Et | H | Me |
| 1.139 | H | H | bond | Cl | H | n-Pr | H | Me |
| 1.140 | H | H | bond | Cl | H | i-Pr | H | Me |
| 1.141 | H | H | bond | Cl | H | c-Pr | H | Me |
| 1.142 | H | H | bond | Cl | H | n-Bu | H | Me |
| 1.143 | H | H | bond | Cl | H | i-Bu | H | Me |
| 1.144 | H | H | bond | Cl | H | c-Bu | H | Me |
| 1.145 | H | H | bond | Cl | H | t-Bu | H | Me |
| 1.146 | H | H | bond | Cl | H | n-Hex | H | Me |
| 1.147 | H | H | bond | Cl | H | CH=NOMe | H | Me |
| 1.148 | H | H | bond | Cl | H | CH=NOEt | H | Me |
| 1.149 | H | H | bond | Cl | H | CH=NO—n-Pr | H | Me |
| 1.150 | H | H | bond | Cl | H | C(Me)=NOMe | H | Me |
| 1.151 | H | H | bond | Cl | H | C(Me)=NOEt | H | Me |
| 1.152 | H | H | bond | Br | H | H | H | Br |
| 1.153 | H | H | bond | Br | H | Cl | H | Br |
| 1.154 | H | H | bond | Br | H | Br | H | Br |
| 1.155 | H | H | bond | Br | H | I | H | Br |
| 1.156 | H | H | bond | Br | H | CHF₂ | H | Br |
| 1.157 | H | H | bond | Br | H | CF₃ | H | Br |
| 1.158 | H | H | bond | Br | H | Me | H | Br |
| 1.159 | H | H | bond | Br | H | Et | H | Br |
| 1.160 | H | H | bond | Br | H | n-Pr | H | Br |
| 1.161 | H | H | bond | Br | H | i-Pr | H | Br |

TABLE 1-continued

| Cpd No. | R$_1$ | R$_2$ | G | R$_9$ | R$_{10}$ | R$_{11}$ | R$_{12}$ | R$_{13}$ |
|---|---|---|---|---|---|---|---|---|
| 1.162 | H | H | bond | Br | H | c-Pr | H | Br |
| 1.163 | H | H | bond | Br | H | n-Bu | H | Br |
| 1.164 | H | H | bond | Br | H | i-Bu | H | Br |
| 1.165 | H | H | bond | Br | H | c-Bu | H | Br |
| 1.166 | H | H | bond | Br | H | t-Bu | H | Br |
| 1.167 | H | H | bond | Br | H | n-Hex | H | Br |
| 1.168 | H | H | bond | Br | H | CH=NOMe | H | Br |
| 1.169 | H | H | bond | Br | H | CH=NOEt | H | Br |
| 1.170 | H | H | bond | Br | H | CH=NO—n-Pr | H | Br |
| 1.171 | H | H | bond | Br | H | C(Me)=NOMe | H | Br |
| 1.172 | H | H | bond | Br | H | C(Me)=NOEt | H | Br |
| 1.173 | H | H | bond | Me | H | H | H | Me |
| 1.174 | H | H | bond | Me | H | Cl | H | Me |
| 1.175 | H | H | bond | Me | H | Br | H | Me |
| 1.176 | H | H | bond | Me | H | I | H | Me |
| 1.177 | H | H | bond | Me | H | CHF$_2$ | H | Me |
| 1.178 | H | H | bond | Me | H | CF$_3$ | H | Me |
| 1.179 | H | H | bond | Me | H | Me | H | Me |
| 1.180 | H | H | bond | Me | H | Et | H | Me |
| 1.181 | H | H | bond | Me | H | n-Pr | H | Me |
| 1.182 | H | H | bond | Me | H | i-Pr | H | Me |
| 1.183 | H | H | bond | Me | H | c-Pr | H | Me |
| 1.184 | H | H | bond | Me | H | n-Bu | H | Me |
| 1.185 | H | H | bond | Me | H | i-Bu | H | Me |
| 1.186 | H | H | bond | Me | H | c-Bu | H | Me |
| 1.187 | H | H | bond | Me | H | t-Bu | H | Me |
| 1.188 | H | H | bond | Me | H | n-Hex | H | Me |
| 1.189 | H | H | bond | Me | H | CH=NOMe | H | Me |
| 1.190 | H | H | bond | Me | H | CH=NOEt | H | Me |
| 1.191 | H | H | bond | Me | H | CH=NO—n-Pr | H | Me |
| 1.192 | H | H | bond | Me | H | C(Me)=NOMe | H | Me |
| 1.193 | H | H | bond | Me | H | C(Me)=NOEt | H | Me |
| 1.194 | H | H | bond | Cl | H | H | H | H |
| 1.195 | H | H | bond | Cl | H | Cl | H | H |
| 1.196 | H | H | bond | Cl | H | Br | H | H |
| 1.197 | H | H | bond | Cl | H | I | H | H |
| 1.198 | H | H | bond | Cl | H | CHF$_2$ | H | H |
| 1.199 | H | H | bond | Cl | H | CF$_3$ | H | H |
| 1.200 | H | H | bond | Cl | H | Me | H | H |
| 1.201 | H | H | bond | Cl | H | Et | H | H |
| 1.202 | H | H | bond | Cl | H | n-Pr | H | H |
| 1.203 | H | H | bond | Cl | H | i-Pr | H | H |
| 1.204 | H | H | bond | Cl | H | c-Pr | H | H |
| 1.205 | H | H | bond | Cl | H | n-Bu | H | H |
| 1.206 | H | H | bond | Cl | H | i-Bu | H | H |
| 1.207 | H | H | bond | Cl | H | c-Bu | H | H |
| 1.208 | H | H | bond | Cl | H | t-Bu | H | H |
| 1.209 | H | H | bond | Cl | H | n-Hex | H | H |
| 1.210 | H | H | bond | Cl | H | CH=NOMe | H | H |
| 1.211 | H | H | bond | Cl | H | CH=NOEt | H | H |
| 1.212 | H | H | bond | Cl | H | CH=NO—n-Pr | H | H |
| 1.213 | H | H | bond | Cl | H | C(Me)=NOMe | H | H |
| 1.214 | H | H | bond | Cl | H | C(Me)=NOEt | H | H |
| 1.215 | F | H | bond | H | H | Cl | H | H |
| 1.216 | F | H | bond | Cl | H | H | H | Cl |
| 1.217 | F | H | bond | Cl | H | Cl | H | Cl |
| 1.218 | F | H | bond | Cl | H | Br | H | Cl |
| 1.219 | F | H | bond | Cl | H | I | H | Cl |
| 1.220 | F | H | bond | Cl | H | CHF$_2$ | H | Cl |
| 1.221 | F | H | bond | Cl | H | CF$_3$ | H | Cl |
| 1.222 | F | H | bond | Cl | H | Me | H | Cl |
| 1.223 | F | H | bond | Cl | H | Et | H | Cl |
| 1.224 | F | H | bond | Cl | H | n-Pr | H | Cl |
| 1.225 | F | H | bond | Cl | H | i-Pr | H | Cl |
| 1.226 | F | H | bond | Cl | H | c-Pr | H | Cl |
| 1.227 | F | H | bond | Cl | H | n-Bu | H | Cl |
| 1.228 | F | H | bond | Cl | H | i-Bu | H | Cl |
| 1.229 | F | H | bond | Cl | H | c-Bu | H | Cl |
| 1.230 | F | H | bond | Cl | H | t-Bu | H | Cl |
| 1.231 | F | H | bond | Cl | H | n-Hex | H | Cl |
| 1.232 | F | H | bond | Cl | H | CH=NOMe | H | Cl |
| 1.233 | F | H | bond | Cl | H | CH=NOEt | H | Cl |
| 1.234 | F | H | bond | Cl | H | CH=NO—n-Pr | H | Cl |
| 1.235 | F | H | bond | Cl | H | C(Me)=NOMe | H | Cl |
| 1.236 | F | H | bond | Cl | H | C(Me)=NOEt | H | Cl |
| 1.237 | OH | H | bond | H | H | Cl | H | H |
| 1.238 | OH | H | bond | Cl | H | H | H | H |
| 1.239 | OH | H | bond | Cl | H | Cl | H | Cl |
| 1.240 | OH | H | bond | Cl | H | Br | H | Cl |
| 1.241 | OH | H | bond | Cl | H | I | H | Cl |
| 1.242 | OH | H | bond | Cl | H | CHF$_2$ | H | Cl |
| 1.243 | OH | H | bond | Cl | H | CF$_3$ | H | Cl |
| 1.244 | OH | H | bond | Cl | H | Me | H | Cl |
| 1.245 | OH | H | bond | Cl | H | Et | H | Cl |
| 1.246 | OH | H | bond | Cl | H | n-Pr | H | Cl |
| 1.247 | OH | H | bond | Cl | H | i-Pr | H | Cl |
| 1.248 | OH | H | bond | Cl | H | c-Pr | H | Cl |
| 1.249 | OH | H | bond | Cl | H | n-Bu | H | Cl |
| 1.250 | OH | H | bond | Cl | H | i-Bu | H | Cl |
| 1.251 | OH | H | bond | Cl | H | c-Bu | H | Cl |
| 1.252 | OH | H | bond | Cl | H | t-Bu | H | Cl |
| 1.253 | OH | H | bond | Cl | H | n-Hex | H | Cl |
| 1.254 | OH | H | bond | Cl | H | CH=NOMe | H | Cl |
| 1.255 | OH | H | bond | Cl | H | CH=NOEt | H | Cl |
| 1.256 | OH | H | bond | Cl | H | CH=NO—n-Pr | H | Cl |
| 1.247 | OH | H | bond | Cl | H | C(Me)=NOMe | H | Cl |
| 1.258 | OH | H | bond | Cl | H | C(Me)=NOEt | H | Cl |
| 1.259 | =O | | bond | H | H | Cl | H | H |
| 1.260 | =O | | bond | Cl | H | H | H | H |
| 1.261 | =O | | bond | Cl | H | Cl | H | Cl |
| 1.262 | =O | | bond | Cl | H | Br | H | Cl |
| 1.263 | =O | | bond | Cl | H | I | H | Cl |
| 1.264 | =O | | bond | Cl | H | CHF$_2$ | H | Cl |
| 1.265 | =O | | bond | Cl | H | CF$_3$ | H | Cl |
| 1.266 | =O | | bond | Cl | H | Me | H | Cl |
| 1.267 | =O | | bond | Cl | H | Et | H | Cl |
| 1.268 | =O | | bond | Cl | H | n-Pr | H | Cl |
| 1.269 | =O | | bond | Cl | H | i-Pr | H | Cl |
| 1.270 | =O | | bond | Cl | H | c-Pr | H | Cl |
| 1.271 | =O | | bond | Cl | H | n-Bu | H | Cl |
| 1.272 | =O | | bond | Cl | H | i-Bu | H | Cl |
| 1.273 | =O | | bond | Cl | H | c-Bu | H | Cl |
| 1.274 | =O | | bond | Cl | H | t-Bu | H | Cl |
| 1.275 | =O | | bond | Cl | H | n-Hex | H | Cl |
| 1.276 | =O | | bond | Cl | H | CH=NOMe | H | Cl |
| 1.277 | =O | | bond | Cl | H | CH=NOEt | H | Cl |
| 1.278 | =O | | bond | Cl | H | CH=NO—n-Pr | H | Cl |
| 1.279 | =O | | bond | Cl | H | C(Me)=NOMe | H | Cl |
| 1.280 | =O | | bond | Cl | H | C(Me)=NOEt | H | Cl |
| 1.281 | C=NOMe | | bond | H | H | Cl | H | H |
| 1.282 | C=NOMe | | bond | Cl | H | H | H | H |
| 1.283 | C=NOMe | | bond | Cl | H | Cl | H | Cl |
| 1.284 | C=NOMe | | bond | Cl | H | Br | H | Cl |
| 1.285 | C=NOMe | | bond | Cl | H | I | H | Cl |
| 1.286 | C=NOMe | | bond | Cl | H | CHF$_2$ | H | Cl |
| 1.287 | C=NOMe | | bond | Cl | H | CF$_3$ | H | Cl |
| 1.288 | C=NOMe | | bond | Cl | H | Me | H | Cl |
| 1.289 | C=NOMe | | bond | Cl | H | Et | H | Cl |
| 1.290 | C=NOMe | | bond | Cl | H | n-Pr | H | Cl |
| 1.291 | C=NOMe | | bond | Cl | H | i-Pr | H | Cl |
| 1.292 | C=NOMe | | bond | Cl | H | c-Pr | H | Cl |
| 1.293 | C=NOMe | | bond | Cl | H | n-Bu | H | Cl |
| 1.294 | C=NOMe | | bond | Cl | H | i-Bu | H | Cl |
| 1.295 | C=NOMe | | bond | Cl | H | c-Bu | H | Cl |
| 1.296 | C=NOMe | | bond | Cl | H | t-Bu | H | Cl |
| 1.297 | C=NOMe | | bond | Cl | H | n-Hex | H | Cl |
| 1.298 | C=NOMe | | bond | Cl | H | CH=NOMe | H | Cl |
| 1.299 | C=NOMe | | bond | Cl | H | CH=NOEt | H | Cl |
| 1.300 | C=NOMe | | bond | Cl | H | CH=NO—n-Pr | H | Cl |
| 1.301 | C=NOMe | | bond | Cl | H | C(Me)=NOMe | H | Cl |
| 1.302 | C=NOMe | | bond | Cl | H | C(Me)=NOEt | H | Cl |

Table 2: Compounds of Formula Ia:

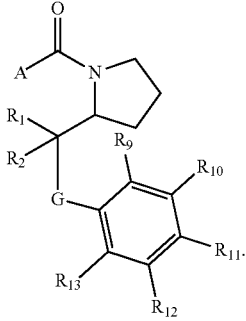

wherein A is the group $A_2$,

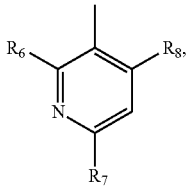

wherein $R_6$ is chloro, $R_7$ is hydrogen and $R_8$ is hydrogen. The remaining substituent definitions of Table 2 correspond to Table 1 above. The individual compounds are numbered accordingly. For example, compound 2.006 of Table 2 corresponds to compound 1.006 with the exeption of the meaning of the substituent "A":

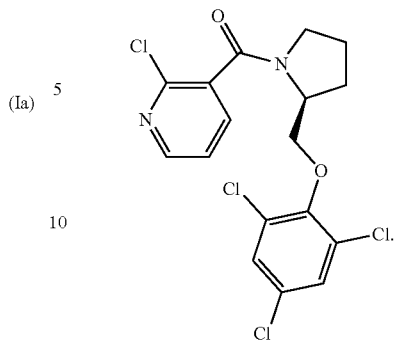

(compound 2.006)

Table 3: Characterising Data

Table 3 shows selected melting point and selected NMR data for compounds of Table 1. $CDCl_3$ was used as the solvent for NMR measurements, unless otherwise stated. If a mixture of solvents was present, this is indicated as, for example: $CDCl_3/d_6$-DMSO). No attempt is made to list all characterising data in all cases.

In Table 3 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

LCMS-data for physico-chemical characterization were obtained on an analytical Waters LC-MS instrument (W2790, ZQ-2000). Column was an Atlantis dC18, 3 um 3.0 mm×20 mm. Solvents were: A=0.1% formic acid in water, B=0.1% formic acid in acetonitrile. Gradient was 20% to 80% B in 2.9 min; flow rate was 1.7 ml/min. Physicochemical data are reported in the following format: retention time (min); M found in positive ionisation mode (m/z$^+$).

TABLE 3

| Cpd No. | 1H-NMR data: ppm (multiplicity/number of Hs) | MS [M + H]$^+$ | m.p. (° C.) | LCMS data |
|---|---|---|---|---|
| 1.005 | | | | 1.46 min; 403 |
| 1.006 | 1.92-1.99 (m, 1H), 2.16-2.22 (m, 2H), 2.38-2.46 (m, 1H), 3.64-3.69 (m, 2H), 3.96 (s, 3H, NCH$_3$), 4.18-4.22 (m, 1H), 4.31-4.34 (m, 1H), 4.59-4.62 (m, 1H), 6.96-7.24 (t, 1H, CHF$_2$), 7.28 (s, 2H, Ar—H), 7.60 (s, 1H) | 438/440/442 | resin | 1.67 min; 437 |
| 1.007 | | | | 1.70 min; 480 |
| 1.008 | | | | 1.75 min; 528 |
| 1.011 | | | | 1.61 min; 417 |
| 1.021 | 1.95 (m, 1H), 2.20 (m, 2H), 2.45 (m, 1H), 3.68 (m, 2H), 3.96 (s, 3H, NCH$_3$), 3.98 (s, 3H, OCH$_3$), 4.22-4.24 (m, 1H), 4.38 (m, 1H), 4.61 (m, 1H), 7.01-7.28 (t, 1H, CHF$_2$), 7.50 (s, 2H, Ar—H), 7.61 (s, 1H), 7.89 (s, 1H) | 361/363/365 | resin | — |
| 1.026 | | | | 1.55 min; 383 |
| 1.027 | | | | 1.65 min; 417 |
| 1.032 | | | | 1.59 min; 397 |
| 1.048 | | | | 1.72 min; 524 |
| 1.050 | | | | 1.79 min; 616 |
| 1.052 | | | | 1.75 min; 558 |
| 1.054 | | | | 1.77 min; 519 |
| 1.055 | | | | 1.90 min; 533 |

TABLE 3-continued

| Cpd No. | 1H-NMR data: ppm (multiplicity/number of Hs) | MS [M + H]$^+$ | m.p. (° C.) | LCMS data |
|---|---|---|---|---|
| 1.061 | | | | 1.94 min; 547 |
| 1.068 | 1.92-1.99 (m, 1H), 2.15-2.24 (m, 2H), 2.22 (s, 6H, 2 × CH$_3$), 2.38-2.46 (m, 1H), 3.62-3.70 (m, 2H), 3.85-3.94 (m, 1H), 3.96 (s, 3H, NCH$_3$), 4.09-4.12 (m, 1H), 4.59-4.62 (m, 1H), 6.90-7.15 (m, 3H, Ar—H, t, 1H, CHF$_2$), 7.60 (s, 1H) | 364 | 137-140 | — |
| 1.074 | | | | 1.56 min; 377 |
| 1.110 | 1.74-2.29 (m, 4H), 2.94-3.80 (m, 4H), 3.85 + 3.97 (s, 3H, NCH$_3$), 4.5 + 4.95 (2m, 1H), 6.60-7.77 (m, 5H, CHF$_2$ + Ar—H) | 388/390/392 | resin | — |
| 1.215 | 1.68-1.73 (m, 1H), 1.73-1.79 (m, 1H), 1.98-2.13 (m, 2H), 3.63-3.71 (m, 2H), 3.97 (s, 3H, NCH$_3$), 4.48-4.59 (2m, 1H), 6.13-6.28 (d, 1H), 6.96-7.23 (t, 1H, CHF$_2$), 7.36 (d × d, 4H, Ar—H), 7.68 (s, 1H) | 372/374 | resin | — |
| 1.237 | 1.51-1.58 (m, 1H), 1.61-1.73 (m, 1H), 1.74-1.84 (m, 2H), 3.49-3.55 (m, 1H), 3.65-3.73 (m, 1H), 3.97 (s, 3H, NCH$_3$), 4.53-4.69 (q, 1H), 4.62-4.69 (d, 1H), 5.82 (s$_{broad}$, 1H), 6.96-7.23 (t, 1H, CHF$_2$), 7.33 (d × d, 4H, Ar—H), 7.64 (s, 1H) | 370/372 | resin | — |
| 1.259 | 1.91-1.98 (m, 1H), 2.02-2.16 (m, 2H), 2.33-2.42 (m, 1H), 3.75-3.85 (m, 2H), 3.97 (s, 3H, NCH$_3$), 5.61-5.65 (m, 1H), 6.99-7.28 (t, 1H, CHF$_2$), 7.45-7.47 (d, 2H, Ar—H), 7.73 (s, 1H) 7.96-7.98 (d, 2H, Ar—H) | 368/370 | resin | — |
| 1.281 | 1.68-1.73 (m, 1H), 1.73-1.79 (m, 1H), 1.98-2.13 (m, 2H), 3.63-3.71 (m, 2H), 3.97 (s, 3H, NCH$_3$), 4.03 (s, 3H, OCH$_3$), 4.48-4.59 (2m, 1H), 6.13-6.28 (d, 1H), 6.96-7.23 (t, 1H, CHF$_2$), 7.36 (d × d, 4H, Ar—H), 7.68 (s, 1H) | 397/399 | resin | — |
| 2.006 | 1.88-1.97 (m, 1H), 2.10-2.28 (m, 2H), 2.47-2.54 (m, 1H), 3.30-3.41 (m, 2H), 4.21-4.24 (m, 1H), 4.44 (m, 1H), 4.60-4.65 (m, 1H), 7.26 (s, 2H, Ar—H), 7.30-7.34 (m, 1H, Py—H), 7.68-7.72 (m, 1H, Py—H), 8.42-8.44 (m, 1H, Py—H). MS [M + H]$^+$ 419/421/423/425. | | oil | |

Formulation Examples for Compounds of Formula I

Example F-1.1 to F-1.2

Emulsifiable Concentrates

| Components | F-1.1 | F-1.2 |
|---|---|---|
| compound of Table 1 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Table 1 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Table 1 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Table 1 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Table 1 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Table 1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Table 1 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples

Fungicidal Actions

Example B-1

Action Against *Botrytis cinerea*—Fungal Growth Assay

Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 3-4 days. The activity of a compound is expressed as fungal growth inhibition (0=no growth inhibition, ratings of 80% to 99% mean good to very good inhibition, 100%=complete inhibition).

Compounds 1.005, 1.006, 1.007, 1.008, 1.011, 1.021, 1.026, 1.027, 1.032, 1.048, 1.050, 1.052, 1.054, 1.055, 1.061 and 1.068 show very good activity in this test (≥80% inhibition).

Example B-2

Action Against *Mycosphaerella arachidis* (Early Leaf Spot of Groundnut; *Cercospora arachidicola* [anamorph])—Fungal Growth Assay Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 6-7 days. The activity of a compound is expressed as fungal growth inhibition (0=no growth inhibition, ratings of 80% to 99% mean good to very good inhibition, 100%=complete inhibition).

Compounds 1.005, 1.006, 1.007, 1.008, 1.011, 1.021, 1.026, 1.027, 1.032, 1.048, 1.050, 1.052, 1.054, 1.055, 1.061, 1.068, 1.074, 1.110 and 1.215 show very good activity in this test (≥80% inhibition).

Example B-3

Action Against *Septoria tritici*—Fungal Growth Assay

Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is determined photometrically after 72 hrs. The activity of a compound is expressed as fungal growth inhibition (0=no growth inhibition, ratings of 80% to 99% mean good to very good inhibition, 100%=complete inhibition).

Compounds 1.005, 1.006, 1.007, 1.008, 1.011, 1.021, 1.026, 1.027, 1.032, 1.048, 1.050, 1.052, 1.054, 1.055, 1.061, 1.068, 1.074, 1.110 and 1.215 show very good activity in this test (≥80% inhibition).

Example B-4

Action Against *Monographella nivalis* (Anamorph: *Fusarium nivale*, *Microdochium nivale*; Snow Mould)—Fungal Growth Assay Conidia of the fungus from cryogenic storage are directly mixed into nutrient broth (PDB potato dextrose broth). After placing a DMSO-solution of the test compounds (0.002% active ingredient) into a microtiter plate (96-well format) the nutrient broth containing the fungal spores is added. The test plates are incubated at 24° C. and the inhibition of growth is measured photometrically after 72 hrs (0=no growth inhibition, ratings of 80% to 99% mean good to very good inhibition, 100%=complete inhibition).

Compounds 1.006 and 1.050 show good activity in this test (≥50% inhibition).

Example B-5

Action Against *Rhizoctonia solani*—Fungal Growth Assay

Mycelial fragments of a newly grown liquid culture of the fungus are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 3-4 days. The activity of a compound is expressed as fungal growth inhibition (0=no growth inhibition, ratings of 80% to 99% mean good to very good inhibition, 100%=complete inhibition).

Compounds 1.006, 1.011, 1.021, 1.027, 1.032, 1.048, 1.050, 1.052, 1.054, 1.055, 1.061 and 1.068 show very good activity in this test (≥50% inhibition).

Example B-6

Action Against *Erysiphe graminis* f.sp. *tritici* (Wheat Powdery Mildew)

Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 7 days after inoculation as preventive fungicidal activity.

Compounds 1.005, 1.006, 1.008, 1.026, 1.027, 1.032, 1.048, 1.050, 1.052 and 1.068 show very good activity in this test (≥80% inhibition). Compound 1.110 shows good activity in this test (≥50% inhibition).

Example B-7

Protective Action Against *Puccinia recondita* (Brown Rust) on Wheat

Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 8 days after inoculation as preventive fungicidal activity.

Compounds 1.005, 1.006, 1.007, 1.008, 1.011, 1.021, 1.027, 1.032, 1.048, 1.050, 1.052, 1.054, 1.055, 1.061, 1.068 and 1.074, show very good activity in this test (≥80% inhibition).

Example B-8

Curative Action Against *Puccinia recondita* (Brown Rust) on Wheat

Wheat leaf segments are placed on agar in multiwell plates (24-well format) and inoculated with a spore suspension of the fungus. One day after inoculation the leaf segments are sprayed with test solutions (0.02% active ingredient). After appropriate incubation the activity of a compound is assessed 8 days after inoculation as curative fungicidal activity.

Compounds 1.006, 1.007, 1.027, 1.052, 1.055 and 1.068 show very good activity in this test (≥80% inhibition).

Example B-9

Action Against *Leptosphaeria nodorum* (*Septoria nodorum*; Glume Blotch) on Wheat Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 4 days after inoculation as preventive fungicidal activity.

Compounds 1.006, 1.068 and 1.215 show good activity in this test (≥50% inhibition).

Example B-10

Action Against *Pyrenophora teres* (Net Blotch) on Barley

Barley leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 4 days after inoculation as preventive fungicidal activity.

Compounds 1.006, 1.007, 1.008, 1.021, 1.026, 1.027, 1.032, 1.048, 1.050, 1.052, 1.055, 1.061, 1.068, 1.074, 1.110 and 1.215 show very good activity in this test (≥80% inhibition). Compound 1.259 shows good activity in this test (≥50% inhibition).

What is claimed is:
1. A compound of formula I

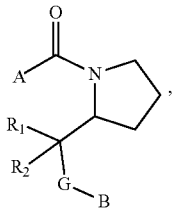
(I)

wherein
A is the group $A_1$

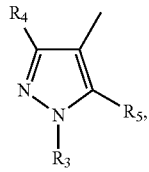
($A_1$)

wherein R1 and R2 independently of each other, are hydrogen, hydroxy, halogen or C1-C6alkyl; or R1 and R2 together is C=O or C=N(O—C1-C6alkyl)
$R_3$ is methyl; $R_4$ is $C_1$-$C_4$haloalkyl and $R_5$ is hydrogen;
B is phenyl which can be substituted by one or more substituents selected from the group consisting of halogen, $C_1$-$C_6$alkyl, $C_3$-$C_6$cycloalkyl, $C_1$-$C_6$haloalkyl, —C($C_1$-$C_4$alkyl)=N—O—$C_1$-$C_6$alkyl or —C(H)=N—O—$C_1$-$C_6$alkyl; and
G is oxygen, sulphur, $CH_2$, $(CH_2)_2$ or a bond;
or a tautomer/isomer/enantiomer thereof.

2. A compound of formula I according to claim 1, represented by the compound of formula Ia,

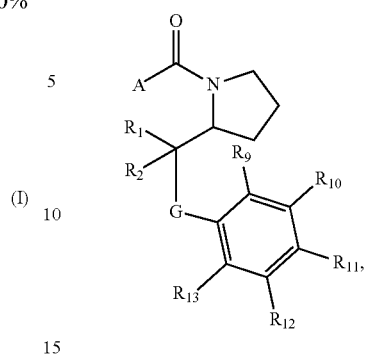
(Ia)

wherein
A, $R_1$, $R_2$ and G are as defined under formula I in claim 1 and $R_9$, $R_{10}$, $R_{11}$, $R_{12}$ and $R_{13}$ independently from each other, are hydrogen, halogen, $C_1$-$C_6$alkyl, $C_1$-$C_6$haloalkyl or C(H)NO—$C_1$-$C_6$alkyl.

3. A compound according to claim 2, wherein $R_9$, $R_{10}$, $R_{11}$, $R_{12}$ and $R_{13}$ independently from each other, are hydrogen, halogen, $C_1$-$C_6$alkyl or C(H)NO—$C_1$-$C_6$alkyl.

4. A compound according to claim 2, wherein $R_1$ and $R_2$ independently of each other, are hydrogen, hydroxy or $R_1$ and $R_2$ together is C=O or C=N(O—$C_1$-$C_6$alkyl).

5. A compound according to claim 2, wherein G is oxygen or a bond.

6. A compound according to claim 1, wherein $R_1$ and $R_2$ are hydrogen.

7. A compound according to claim 1, wherein $R_1$ and $R_2$ together are C=O or C=N(O—$C_1$-$C_6$alkyl).

8. A compound according to claim 1, wherein G is oxygen or a bond.

9. A compound according to claim 1, wherein G is oxygen.

10. A method of controlling or preventing infestation of useful plants by phytopathogenic microorganisms, wherein a compound of formula I according to claim 1 or a composition, comprising this compound as active ingredient, is applied to the plants, to parts thereof or the locus thereof.

11. A composition for controlling and protecting against phytopathogenic microorganisms, comprising a compound of formula I according to claim 1 and an inert carrier.

* * * * *